United States Patent
Shinobu et al.

(10) Patent No.: US 8,053,461 B2
(45) Date of Patent: Nov. 8, 2011

(54) OXINDOLE DERIVATIVE

(75) Inventors: Noriaki Shinobu, Sapporo (JP); Jun Shao, Sapporo (JP); Masataka Kobayashi, Sapporo (JP); Takao Mori, Sapporo (JP)

(73) Assignee: Theravalues Corporation, Tokyo (JP)

( * ) Notice: Subject to any disclaimer, the term of this patent is extended or adjusted under 35 U.S.C. 154(b) by 107 days.

(21) Appl. No.: 12/513,332

(22) PCT Filed: Nov. 5, 2007

(86) PCT No.: PCT/JP2007/071503
§ 371 (c)(1),
(2), (4) Date: May 1, 2009

(87) PCT Pub. No.: WO2008/056634
PCT Pub. Date: May 15, 2008

(65) Prior Publication Data
US 2010/0076049 A1    Mar. 25, 2010

(30) Foreign Application Priority Data
Nov. 6, 2006 (JP) .................................. 2006-300938

(51) Int. Cl.
*A61K 31/40* (2006.01)
(52) U.S. Cl. ....................................................... 514/414
(58) Field of Classification Search .................. 514/183, 514/414
See application file for complete search history.

(56) References Cited

U.S. PATENT DOCUMENTS

2003/0219380 A1    11/2003    Fong et al.

FOREIGN PATENT DOCUMENTS

| JP | 2003-523340 A | 8/2003 |
|---|---|---|
| WO | WO 01/60814 A2 | 8/2001 |
| WO | WO 02/081466 A1 | 10/2002 |
| WO | WO 2005/058309 A1 | 6/2005 |

OTHER PUBLICATIONS

Janne et al 'Factors underlying sensitivity of cancers to small-molecule kinase inhibitors' Nature Reviews: Drug Discovery, vol. 8, p. 709-723, 2009.*
Suggitt et al '50 Years of Preclinical Anticancer Drug Screening: Empirical to Target-Driven Approaches' Clinical Cancer Research, vol. 11, p. 971-981, 2005.*
Cuypers, H. Theo, et al. Murine Leukemia Virus-Induced T-Cell Lymphomagenesis: Integration of Proviruses in a Distinct Chromosomal Region; Cell, May 1984, pp. 141-150, vol. 37.
Selten, Gerard, et al. "Proviral Activation of the Putative Oncogene Pim-1 in MuLV induced T-cell lymphomas." The EMBO Journal, 1985 pp. 1793-1798, vol. 4 No. 7.
Bachmann, Malte, et al. "The Serine/threonine Kinase Pim-1." The International Journal of Biochemistry & Cell Biology, 2005, pp. 726-730, vol. 37.
Chifumi Fujii, et al. "Aberrant Expression of Serine/Threonine Kinase Pim-3 in hepatocellular carcinoma development and its role in the proliferation of human hepatoma cell lines." International J. Cancer, 2005, pp. 209-218, vol. 114.
Li, Ying-Yi, et al. "Pim-3, a Proto-Oncogene with Serine/Threonine Kinase Activity, Is Aberrantly Expressed in Human Pancreatic Cancer and Phosphorylates Bad to Block Bad-Mediated Apoptosis in Human Pancreatic Cancer Cell Lines." Cancer Research. Jul. 1, 2006, pp. 6741-6747, vol. 66(13).
Mologni, Luca et al. Inhibition of RET Tyrosine Kinase by SU5416, Journal of Molecular Endocrinolgy, 2006, pp. 199-212, vol. 37, No. 2.
Accession No. (AN): 203127644 Chemcasts Catalog Name (CO): Aurora Screening Library Publication Date (PD): Jan. 1, 2007 Order Number (ON): kmy-026850 Chemical Name (CN): 1H-Isoindole-1, 3 (2H)-dione, 1-[[5-[(1,2-dihydro-2-oxo-3H-indol-3-ylidene) methyl]-2-furanyl]methyl]- CAS Registry No. (RN): 697741-84-7, Supplemetary Term (ST) Chemical Library.

* cited by examiner

*Primary Examiner* — Brandon Fetterolf
*Assistant Examiner* — Christopher R Stone
(74) *Attorney, Agent, or Firm* — Arent Fox, LLP

(57) ABSTRACT

A compound or a pharmaceutically acceptable salt thereof of the present invention is represented by the following general formula (I):

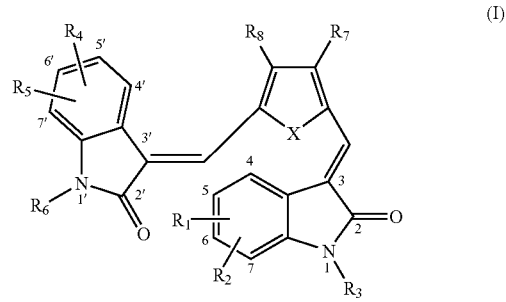

[wherein, $R_1$ to $R_8$ may have a hydrogen atom, a halogen atom, a hydroxy group, a C1-C6 alkyl group, a C2-C8 alkenyl group, a C1-C6 alkylcarbonyl group or —$COOR_9$ (wherein $R_9$ represents a hydrogen atom, a C1-C6 alkyl group or a C2-C8 alkenyl group) as a substituent; and X represents a sulfur atom, an oxygen atom or $NR_{10}$ (wherein $R_{10}$ represents a hydrogen atom, a halogen atom, a hydroxy group, a C1-C6 alkyl group, a C2-C8 alkenyl group or a C1-C6 alkoxy group)].

9 Claims, 13 Drawing Sheets

OXINDOLE DERIVATIVE

CROSS-REFERENCE TO RELATED APPLICATION

This application is a National Stage entry of International Application No. PCT/JP2007/071503, filed Nov. 5, 2007, which claims priority to Japanese Application No. 2006-300938, filed Nov. 6, 2006 the disclosure of the prior applications is hereby incorporated in their entirety by reference.

TECHNICAL FIELD

The present invention relates to an oxindole derivative and pharmaceutical use thereof.

BACKGROUND ART

Kinases are enzymes which transfer (phosphorylates) a phosphate group from a molecule having a high energy phosphate bond such as ATP to a substrate or a target molecule. Among them, protein kinases which are enzymes capable of phosphorylating protein molecules function as regulatory factors in various signal transduction pathways or metabolic pathways in cells. Functional abnormality of kinases often causes diseases such as cancer, and it has been expected that an agent having a function to inhibit a specific kinase is developed and the developed agent is used for treatment or prevention of diseases.

A serine/threonine kinase Pim-1 is a serine/threonine kinase which was at first identified as a gene to be often activated by murine leukemia virus (MuLV) insertion in a T-cell lymphoma caused by the leukemia virus (Non-patent document 1). Further, it is reported that Pim-1 in cytoplasm functions as a factor for inhibiting apoptosis in various hematopoietic cells (Non-patent document 2).

It is known that Pim-1 is expressed not only in hematopoietic cells but also in the lymphatic system, prostate gland, testis, and oral epithelial cells. It is also known that the majority of the function of Pim-2 and Pim-3 which are serine/threonine kinases and have significant sequence homology to Pim-1 overlaps with that of Pim-1 (Non-patent document 3).

Further, it is known that Pim-3 is expressed in malignancies in the pancreatic and liver cells, but is not expressed in normal pancreatic tissues, and it is reported that Pim-3 functions as a factor for inhibiting apoptosis in human pancreatic cancer cells and of hepatocellular cancer cell lines (Non-patent documents 4 and 5).

Non-patent document 1: Cuypers, H. T., Selten, G., Quint, W., Zijlstra, M., Maandag, E. R., Boelens, W., van Wezenbeek, P., Melief, C., Berns, A. Murine leukemia virus-induced T-cell lymphomagenesis: integration of proviruses in a distinct chromosomal region. Cell, 37: 141-150, 1984

Non-patent document 2: Selten, G., Cuypers, H. T. & Berns, A. Proviral activation of the putative oncogene Pim-1 in MuLV induced T-cell lymphomas. EMBO J, 4: 1793-1798, 1985

Non-patent document 3: Malte Bachmann, Tarik Moroy, The serine/threonine kinase Pim-1, The International Journal of Biochemistry & Cell Biology 37 (2005) 726-730

Non-patent document 4: Chifumi Fujii, Yasunari Nakamoto, Peirong Lu, Koichi Tsuneyama, Boryana K. Popivanova, Shuichi Kaneko and Naofumi Mukaida, Aberrant expression of serine/threonine kinase Pim-3 in hepatocellular carcinoma development and its role in the proliferation of human hepatoma cell lines, Int. J. Cancer: 114, 209-218 (2005)

Non-patent document 5: Ying-Yi Li, Boryana K. Popivanova, Youichiro Nagai, Hiroshi Ishiokura, Chifumi Fujii, and Naofumi Mukaida, Pim-3, a Proto-Oncogene with Serine/Threonine Kinase Activity, Is Aberrantly Expressed in Human Pancreatic Cancer and Phosphorylates Bad to Block Bad-Mediated Apoptosis in Human Pancreatic Cancer Cell Line, Cancer Res 2006, 66: (13). Jul. 1, 2006; 6741-7

DISCLOSURE OF THE INVENTION

Problems to Be Solved by the Invention

An object of the present invention is to provide a compound or a pharmaceutically acceptable salt thereof useful as an agent for inhibiting kinase activity, and a compound or a pharmaceutically acceptable salt thereof useful as an agent for treating and/or preventing a kinase-related disease such as cancer.

Means for Solving the Problems

The present inventors made intensive studies in order to achieve the above object and as a result, they found that a specific compound or a pharmaceutically acceptable salt thereof capable of inactivating a certain type of kinase such as a Pim kinase effectively works for prevention and/or treatment of various diseases caused by kinases such as solid cancer, and thus, the invention has been completed. That is, the invention includes the following embodiments.

[1] A compound represented by the following general formula (I):

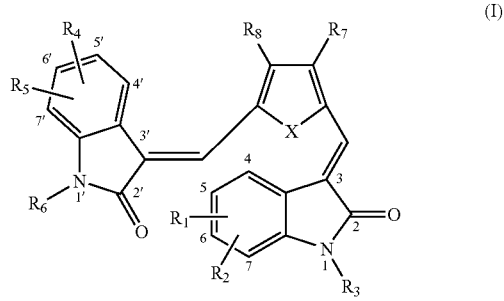

[wherein $R_1$ to $R_8$ may have a hydrogen atom, a halogen atom, a hydroxy group, a C1-C6 alkyl group, a C2-C8 alkenyl group, a C1-C6 alkylcarbonyl group or —$COOR_9$ (wherein $R_9$ represents a hydrogen atom, a C1-C6 alkyl group or a C2-C8 alkenyl group) as a substituent; and X represents a sulfur atom, an oxygen atom or $NR_{10}$ (wherein $R_{10}$ represents a hydrogen atom, a halogen atom, a hydroxy group, a C1-C6 alkyl group, a C2-C8 alkenyl group or a C1-C6 alkoxy group)] or a pharmaceutically acceptable salt thereof.

[2] The compound or a pharmaceutically acceptable salt thereof according to [1], wherein $R_1$, $R_2$, $R_4$ and $R_5$ are each independently a hydrogen atom or $COOR_9$ (wherein $R_9$ represents a hydrogen atom, a C1-C6 alkyl group or a C2-C8 alkenyl group).

[3] The compound or a pharmaceutically acceptable salt thereof according to [1] or [2], wherein $R_3$ and $R_6$ are each independently a hydrogen atom or a C1-C6 alkylcarbonyl group.

[4] The compound or a pharmaceutically acceptable salt thereof according to any one of [1] to [3], wherein $R_7$ and $R_8$ are a hydrogen atom.

[5] The compound or a pharmaceutically acceptable salt thereof according to any one of [1] to [4], wherein X is an oxygen atom.

[6] A compound represented by any of the following formulae (1) to (7):

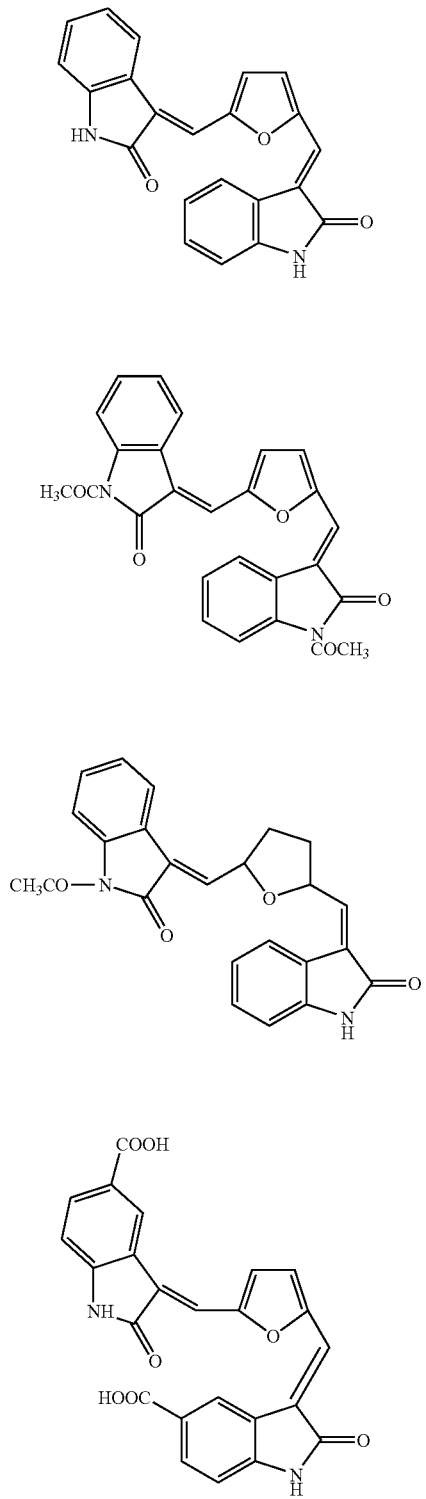

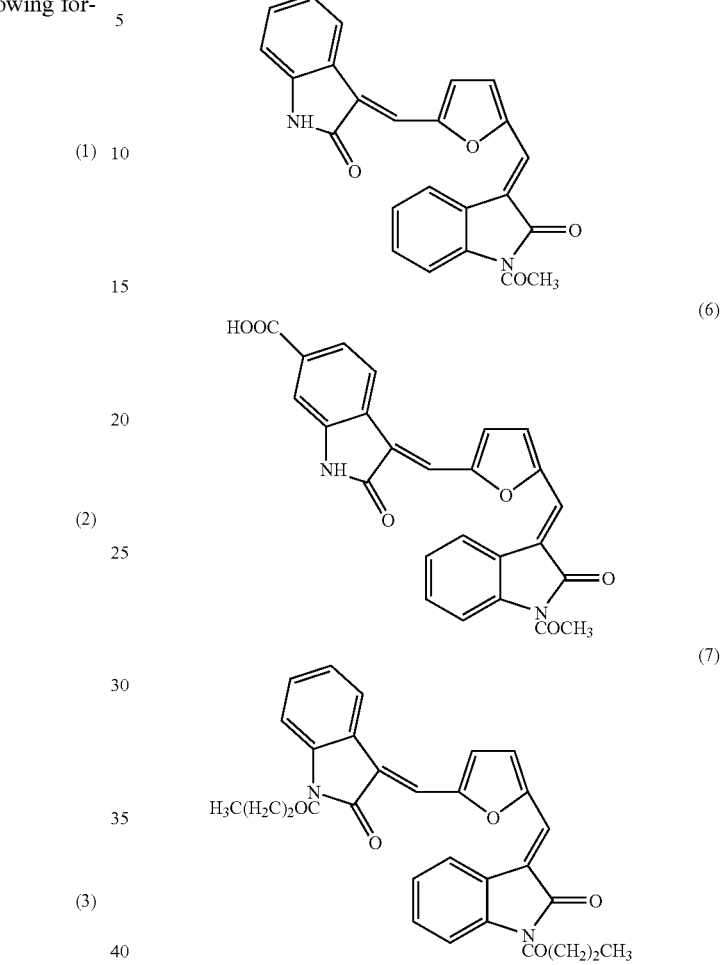

or a pharmaceutically acceptable salt thereof.

[7] A kinase inhibitor comprising the compound or a pharmaceutically acceptable salt thereof according to any one of [1] to [6] as an active ingredient.

[8] The kinase inhibitor according to [7], wherein the kinase inhibitor is a Pim kinase inhibitor.

[9] The kinase inhibitor according to [7] or [8], wherein the kinase inhibitor is an apoptosis inducer.

[10] A preventive and/or therapeutic agent for a kinase-related disease comprising the compound or a pharmaceutically acceptable salt thereof according to any one of [1] to [6] as an active ingredient.

[11] The preventive and/or therapeutic agent according to [10], wherein the kinase-related disease is cancer, a cell proliferation disorder, cardiac disturbance, myocardial infarction, arteriosclerosis, an occlusive cardiovascular disease, rheumatoid arthritis, diabetic retinopathy, age-related macular degeneration retinopathy, a neurodegenerative disease, an autoimmune disease, an inflammatory disease, diabetes or a viral disease.

[12] The preventive and/or therapeutic agent according to [11], wherein the cancer is solid cancer.

[13] A method for preventing and/or treating a kinase-related disease comprising administering an effective amount of the compound or a pharmaceutically acceptable salt thereof according to any one of [1] to [6] to a patient with a kinase-related disease.

[14] Use of the compound or a pharmaceutically acceptable salt thereof according to any one of [1] to [6] for producing a preventive and/or therapeutic agent for a kinase-related disease.

Hereinafter, the meanings of terms, symbols and the like as used herein will be defined and the present invention will be described in detail.

The "kinase activity" as used herein refers to phosphorylation of a target protein by any of various kinases. The "kinase activity" encompasses phosphorylation of a target protein by a serine/threonine kinase and phosphorylation of a target protein by a Pim kinase.

The "Pim kinase" as used herein is a protein having serine/threonine kinase activity and specific examples thereof include Pim-1 kinase, Pim-2 kinase and Pim-3 kinase.

The "Pim-1 kinase" as used herein is a protein having serine/threonine kinase activity identified as a gene to be activated by murine leukemia virus (MuLV) insertion in a T-cell lymphoma caused by MuLV (Cuypers, H. T., Selten, G., Quint, W., Zijlstra, M., Maandag, E. R., Boelens, W., van Wezenbeek, P., Melief, C., Berns, A. Murine leukemia virus-induced T-cell lymphomagenesis: integration of proviruses in a distinct chromosomal region. Cell, 37: 141-150, 1984).

The "Pim-2 kinase" as used herein is a protein having serine/threonine kinase activity identified as a gene to be activated by murine leukemia virus (MuLV) insertion in a T-cell lymphoma caused by MuLV similar to the "Pim-1 kinase" (Andrew Macdonald, David G. Campbell, Rachel Toth, Hilary McLauchlan, C. James Hastie, and J. Simon C. Arthur, BMC Cell Biol. 2006; 7: 1).

The "Pim-3 kinase" as used herein is a protein having serine/threonine kinase activity identified as a gene (KID-1) induced by depolarization in PC12 cells of a rat pheochromocytoma cell line (Feldman J D, Vician L, Crispino M, Tocco G, Marcheselli V L, Bazan N G, Baudry M, Herschman H R., J. of Biol. Chem., 1998, Jun. 26; 273 (26): 16535-43).

The "kinase inhibition" as used herein refers to a function to inhibit phosphorylation of a target protein by any of various kinases. In the case where a reaction of cell apoptosis inhibition is caused subsequent to phosphorylation of a target protein, inhibition of the ability to inhibit apoptosis, i.e., induction of apoptosis is encompassed.

The "serine/threonine kinase inhibition" as used herein refers to a case where in the definition of the kinase inhibition, the kinase is a serine/threonine kinase.

The "Pim kinase inhibition" as used herein refers to a case where in the definition of the kinase inhibition, the kinase is a Pim kinase.

The "kinase inhibitor" as used herein refers to a pharmaceutical composition containing, as an active ingredient, a compound having a function to inhibit phosphorylation of a target protein by a kinase or an ability to induce apoptosis.

The "serine/threonine kinase inhibitor" as used herein refers to a pharmaceutical composition containing, as an active ingredient, a compound having an ability to inhibit a serine/threonine kinase.

The "Pim kinase inhibitor" as used herein refers to a pharmaceutical composition containing, as an active ingredient, a compound having an ability to inhibit a Pim kinase.

In the invention, the "kinase inhibitor" is preferably a "serine/threonine kinase inhibitor", more preferably a "Pim kinase inhibitor", particularly preferably a "Pim-1 activity inhibitor".

The "kinase-related disease" as used herein means a "disease due to kinase activity" and means a disease in which various reactions including at least phosphorylation of a target protein by kinase activity and cell apoptosis inhibition subsequent to the phosphorylation are related to the cause or progression of the disease.

The "Pim-related disease" as used herein means a "disease due to Pim kinase activity" and means a disease in which various reactions including at least phosphorylation of a target protein by Pim kinase activity and cell apoptosis inhibition subsequent to the phosphorylation are related to the cause or progression of the disease.

Specific examples of such a "kinase-related disease" or a "Pim-related disease" include cancer, cell proliferation disorders, cardiac disturbance, myocardial infarction, arteriosclerosis, occlusive cardiovascular diseases, rheumatoid arthritis, diabetic retinopathy, age-related macular degeneration retinopathy, neurodegenerative diseases, autoimmune diseases, inflammatory diseases, diabetes and viral diseases.

The "solid cancer" as used herein refers to all cancer except blood cancer and includes, for example, stomach cancer, lung cancer, breast cancer, esophageal cancer, large bowel cancer, liver cancer, pancreatic cancer, renal cancer, ovarian cancer, uterine cancer, skin cancer, brain tumor, prostate cancer and the like.

The "alkyl group" as used herein is a monovalent group derived by removing one arbitrary hydrogen atom from aliphatic hydrocarbon and does not contain a heteroatom or an unsaturated carbon-carbon bond in the backbone but has a partial assembly of hydrocarbyl or hydrocarbon containing hydrogen and carbon atoms. The alkyl group has a linear or branched structure. The "C1-Cn alkyl group" means that the number of carbon atoms is from 1 to n.

Specific examples thereof include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group and a 2,3-dimethyl-2-butyl group, and preferred is a methyl group.

The "alkenyl group" as used herein is a monovalent group having at least one double bond (two adjacent SP2 carbon atoms). Depending on the placement of a double bond and substituents, if any, the geometry of the double bond may be of the entgegen (E) or zusammen (Z), cis or trans configuration. The "C1-Cn alkenyl group" means that the number of carbon atoms is from 1 to n. As the alkenyl group, a linear or branched alkenyl group can be exemplified.

Specific examples of the alkenyl group include a vinyl group, an allyl group, a 1-propenyl group, a 2-propenyl group, a 1-butenyl group, a 2-butenyl group (including cis and trans forms), a 3-butenyl group, a pentenyl group and a hexenyl group, and preferred is a vinyl group.

The "C1-Cn alkylcarbonyl group" as used herein means a group in which the above-defined "C1-Cn alkyl group" is bound to a carbonyl group. Specific examples thereof include a methylcarbonyl group, an ethylcarbonyl group, a 1-propylcarbonyl group, a 2-propylcarbonyl group, a 2-methyl-1-propylcarbonyl group, a 2-methyl-2-propylcarbonyl group, a 1-butylcarbonyl group, a 2-butylcarbonyl group, a 1-pentylcarbonyl group, a 2-pentylcarbonyl group, a 3-pentylcarbonyl group, a 2-methyl-1-butylcarbonyl group, a 3-methyl-1-butylcarbonyl group, a 2-methyl-2-butylcarbonyl group, a 3-methyl-2-butylcarbonyl group and a 2,2-dimethyl-1-propylcarbonyl group, and preferred is a methylcarbonyl group or a 1-propylcarbonyl group.

The "C1-Cn alkoxy group" as used herein means an oxy group to which the above-defined "C1-Cn alkyl group" is bound. Specific examples thereof include a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group and a 2,3-dimethyl-2-butyloxy group, and preferred is a methoxy group.

The "halogen atom" as used herein means a fluorine atom, a chlorine atom, a bromine atom or an iodine atom, and preferred is a bromine atom.

The "salt" as used herein is not particularly limited as long as it is a salt formed with the compound according to the invention and is pharmacologically acceptable. Examples thereof include inorganic acid salts, organic acid salts, inorganic base salts, organic base salts, and acidic or basic amino acid salts.

Preferred examples of the inorganic acid salts include hydrochlorides, hydrobromides, sulfates, nitrates and phosphates. Preferred examples of the organic acid salts include acetates, succinates, fumarates, maleates, tartrates, citrates, lactates, stearates, benzoates, methanesulfonates, and p-toluenesulfonates.

Preferred examples of the inorganic base salts include alkali metal salts such as sodium salts and potassium salts, alkaline earth metal salts such as calcium salts and magnesium salts, aluminum salts and ammonium salts, and particularly preferred are sodium salts. Preferred examples of the organic base salts include diethylamine salts, diethanolamine salts, meglumine salts and N,N'-dibenzylethylenediamine salts.

Preferred examples of the acidic amino acid salts include aspartates and glutamates. Preferred examples of the basic amino acid salts include arginine salts, lysine salts and ornithine salts.

In this description, the structural formula of a compound may represent a certain isomer for the sake of convenience. However, the invention includes all isomers that occur in the structure of the compound such as geometric isomers, optical isomers based on asymmetric carbons, stereoisomers and tautomers, and mixtures of isomers. The compound of the invention is not limited to the formulae presented for the sake of convenience, and may be any one of the isomers or a mixture thereof. Accordingly, the compound of the invention may have an asymmetric carbon atom in the molecule, and may exist as an optically active compound and a racemate. However, in the invention, the compound is not limited thereto and includes all possible forms. Further, there may be crystalline polymorphisms, however, again, the compound is not limited thereto, and any of the crystal forms may be a single crystal form or the compound may comprise a mixture of crystal forms. Further, the compound according to the invention includes an anhydride and a hydrate. Further, so-called a metabolite which is generated as a result of in vivo metabolism of the compound according to the invention is also included in the scope of claims of the invention.

The compound of the invention and preferred embodiments thereof are as follows.

Compounds represented by the following general formula (I).

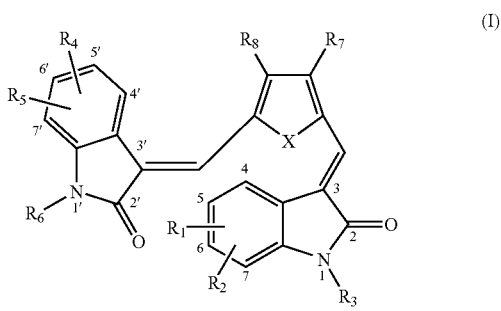

In the formula, $R_1$ to $R_8$ represent a hydrogen atom, a halogen atom, a hydroxy group, a C1-C6 alkyl group, a C2-C8 alkenyl group, a C1-6 alkylcarbonyl group or —$COOR_9$ (wherein $R_9$ represents a hydrogen atom, a C1-C6 alkyl group or a C2-C8 alkenyl group).

$R_1$, $R_2$, $R_4$ and $R_5$ are preferably each independently a hydrogen atom or —$COOR_9$ (wherein $R_9$ represents a hydrogen atom, a C1-C6 alkyl group or a C2-C8 alkenyl group), more preferably each independently a hydrogen atom or —COOH.

When either $R_1$ or $R_4$ is or both are —$COOR_9$, the position of the substituent is preferably at least the 5- or 5'-position, or the 6- or 6'-position in the formula (I).

$R_3$ and $R_6$ are preferably each independently a hydrogen atom or a C1-6 alkylcarbonyl group, more preferably each independently a hydrogen atom, a methylcarbonyl group or a 1-propylcarbonyl group.

$R_7$ and $R_8$ are preferably each independently a hydrogen atom.

In the formula, X represents a sulfur atom, an oxygen atom or $NR_{10}$ (wherein $R_{10}$ represents a hydrogen atom, a halogen atom, a hydroxy group, a C1-C6 alkyl group, a C2-C8 alkenyl group or a C1-C6 alkoxy group), and is preferably an oxygen atom.

In the above formula (I), preferred embodiments of the substituents $R_1$ to $R_8$ are as follows.

(1) $R_1$=$R_2$=$R_4$=$R_5$= a hydrogen atom, $R_3$=$R_6$= a hydrogen atom, $R_7$=$R_8$= a hydrogen atom (2) $R_1$=$R_2$=$R_4$=$R_5$= a hydrogen atom, $R_3$=$R_6$= a C1-6 alkylcarbonyl group, $R_7$=$R_8$= a hydrogen atom (3) $R_1$=$R_2$=$R_4$=$R_5$= a hydrogen atom, $R_3$= a hydrogen atom, $R_6$= a C1-6 alkylcarbonyl group, $R_7$=$R_8$= a hydrogen atom (4) $R_1$=$R_4$=—$COOR_9$ (wherein $R_9$ represents a hydrogen atom, a C1-C6 alkyl group, a C2-C8 alkenyl group or a C1-C6 alkoxy group), $R_2$=$R_5$= a hydrogen atom, $R_3$=$R_6$= a hydrogen atom, $R_7$=$R_8$= a hydrogen atom (5) $R_1=R_2=R_5=$ a hydrogen atom, $R_4=$—$COOR_9$ (wherein $R_9$ represents a hydrogen atom, a C1-C6 alkyl group, a C2-C8 alkenyl group or a C1-C6 alkoxy group), $R_3=$ a C1-6 alkylcarbonyl group, $R_6=$ a hydrogen atom, $R_7=R_8=$ a hydrogen atom As such compounds represented by formula (I), for example, the following compounds (1) to (7) can be specifically exemplified.

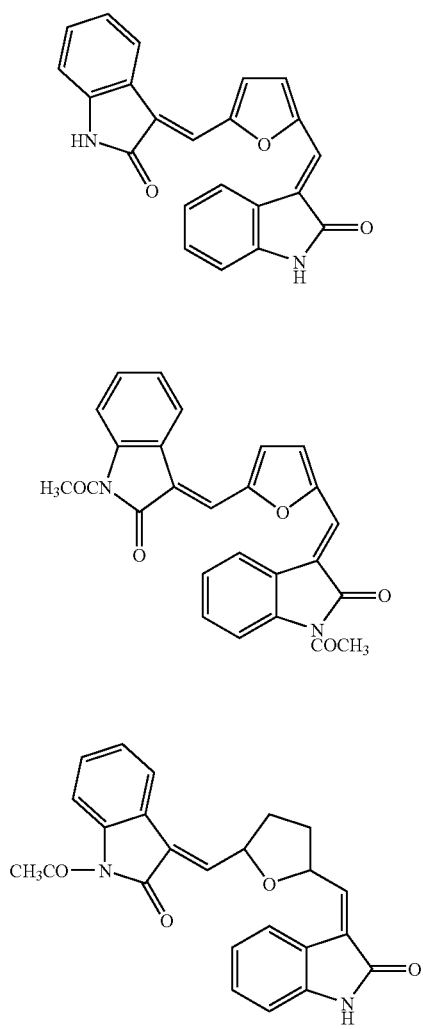

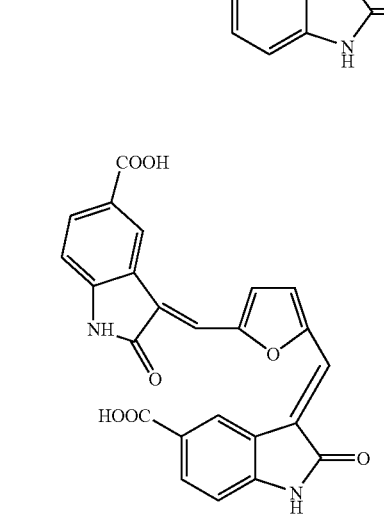

-continued

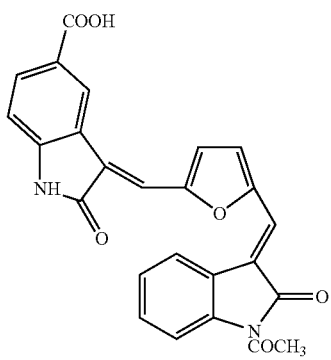

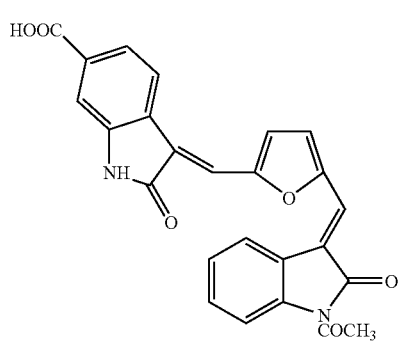

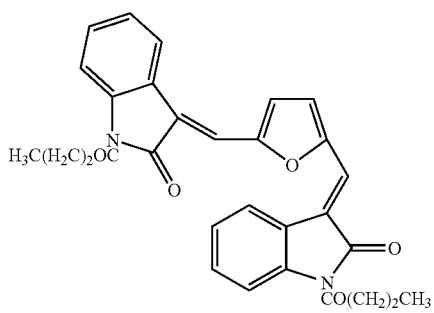

The compounds employed in the invention and preferred compounds thereof can be obtained by, for example, the following synthetic method.

In the following synthesis examples, $R_1$ to $R_8$ and X have the same meanings as the substituents $R_1$ to $R_8$ and X in formula (I) above.

Method A:

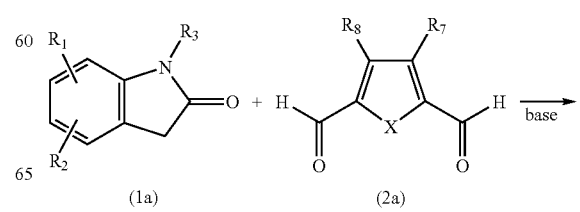

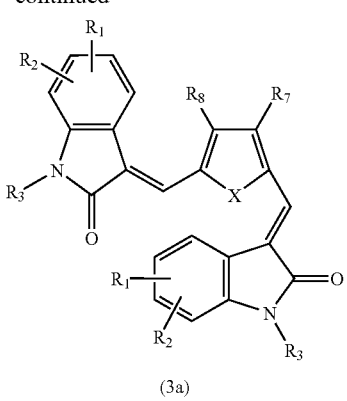

(3a)

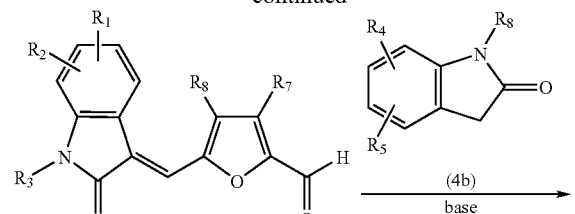

(3b)

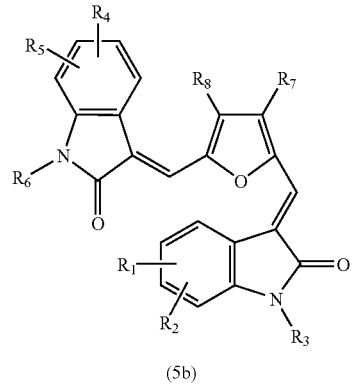

(5b)

In the method A, to an oxindole derivative (1a), a diformylfuran derivative (2a) and a base are added, and the resulting mixture is stirred at −78 to 40° C. for 10 minutes to 72 hours, followed by isolation and purification, whereby a target compound (3a) can be obtained.

A solvent to be used is not particularly limited as long as it is not involved in the reaction, and examples thereof include alcohol solvents such as methanol, ethanol and n-propanol, ether solvents such as THF and dioxane, aromatic solvents such as benzene, toluene and xylene, nitrile solvents such as acetonitrile, halogen solvents such as dichloromethane, dimethyl sulfoxide (DMSO) and dimethyl formamide (DMF), and preferred is ethanol.

Examples of the base to be used include organic bases such as triethylamine, pyridine, piperidine and imidazole, hydrides of alkali metals or alkaline earth metals such as lithium hydride and sodium hydride, alkali metal alkoxides such as sodium methoxide and sodium ethoxide, alkali metal carbonates such as sodium carbonate and potassium carbonate, alkali metal bicarbonates such as sodium bicarbonate and potassium bicarbonate, and alkali metal hydroxides such as sodium hydroxide and potassium hydroxide, and preferred are organic bases, and more preferred is piperidine.

The reaction temperature is usually from −78 to 40° C., preferably from 0 to 30° C.

The reaction time varies depending on the reaction temperature, however, it is usually from 10 minutes to 72 hours, preferably from 24 to 48 hours.

The isolation and purification are performed by employing a common scientific procedure such as extraction, concentration, distillation, crystallization, filtration, recrystallization, or various types of chromatography, however, a preferred procedure is filtration.

Method B:

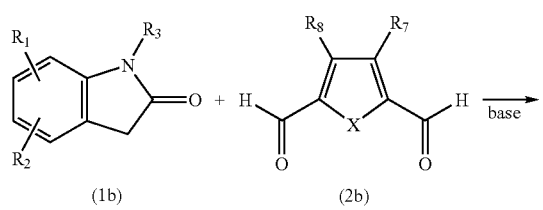

In the method B, a diformylfuran derivative (2b) is dissolved in a solvent, and a solution obtained by dissolving an oxindole derivative (1b) in a solvent is gradually added thereto. After completion of the addition, the resulting mixture is stirred at −78 to 30° C. for 10 minutes to 2 hours, followed by isolation and purification, whereby an intermediate (3b) can be obtained.

Subsequently, in the presence of a solvent, an oxindole derivative (4b) and a base are added to the intermediate (3b), and the resulting mixture is stirred at to 30° C. for 10 minutes to 24 hours, followed by isolation and purification, whereby a target compound (5b) can be obtained.

The solvent to be used is not particularly limited as long as it is not involved in the reaction, and examples thereof include alcohol solvents such as methanol, ethanol and n-propanol, ether solvents such as THF and dioxane, aromatic solvents such as benzene, toluene and xylene, nitrile solvents such as acetonitrile, halogen solvents such as dichloromethane, dimethyl sulfoxide (DMSO) and dimethyl formamide (DMF), and preferred is ethanol.

Examples of the base to be used include organic bases such as triethylamine, pyridine, piperidine and imidazole, hydrides of alkali metals or alkaline earth metals such as lithium hydride and sodium hydride, alkali metal alkoxides such as sodium methoxide and sodium ethoxide, alkali metal carbonates such as sodium carbonate and potassium carbonate, alkali metal bicarbonates such as sodium bicarbonate and potassium bicarbonate, and alkali metal hydroxides such as sodium hydroxide and potassium hydroxide, and preferred are organic bases, and more preferred is piperidine.

The reaction temperature is usually from −78° C. to 40° C., preferably from 0° C. to 30° C.

The reaction time varies depending on the reaction temperature, however, it is usually from 10 minutes to 24 hours, preferably from 6 hours to 18 hours.

The isolation and purification are performed by employing a common scientific procedure such as extraction, concentration, distillation, crystallization, filtration, recrystallization, or various types of chromatography, however, a preferred procedure is filtration.

The oxindole derivative can be synthesized by a common procedure used by a person skilled in the art, and for example, an N-acetyl compound or a carboxyl group-substituted compound can be synthesized by the following method.
Synthesis of N-Acetyl Compound (2c)

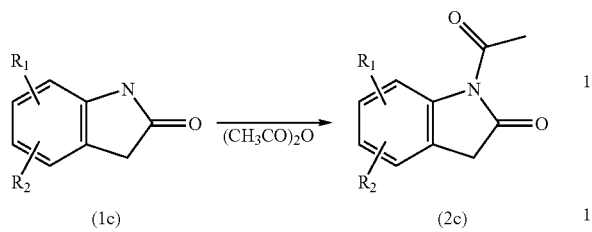

An oxindole derivative (1c) is dissolved in acetic anhydride, and the resulting mixture is refluxed for 24 to 72 hours, followed by isolation and purification, whereby an N-acetyl compound (2c) can be synthesized.

The reaction time varies depending on the reaction temperature, however, it is usually from 10 minutes to 24 hours, preferably from 6 hours to 18 hours.

The isolation and purification are performed by employing a common scientific procedure such as extraction, concentration, distillation, crystallization, filtration, recrystallization, or various types of chromatography, however, a preferred procedure is filtration.
Synthesis of Carboxyl Group-Substituted Compound (3d)

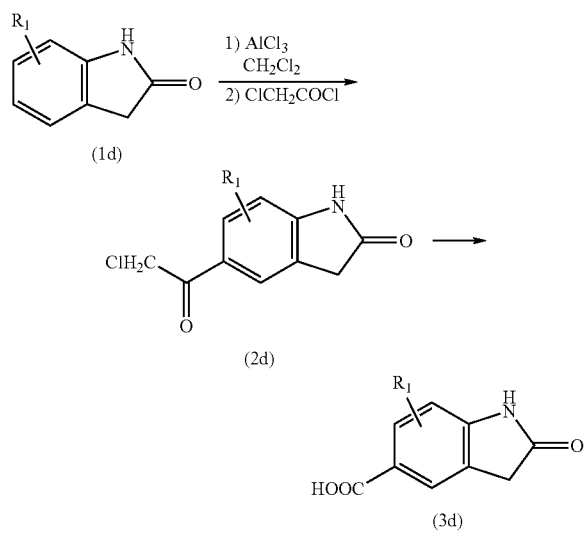

Aluminum chloride (anhydride) is suspended in methylene chloride, and an oxindole derivative (1d) is added to the resulting solution while stirring. To the thus obtained solution, chloroacetyl chloride is added dropwise and stirred, followed by isolation and purification, whereby a chloroacetyl group-substituted compound (2d) can be synthesized. Further, the chloroacetyl group bound to a phenyl group is treated with an alkali according to a common procedure, whereby a carboxyl group-substituted compound (3d) can be obtained.

The reaction temperature is from 0 to 50° C., preferably from 40 to 50° C.

The reaction time varies depending on the reaction temperature, however, it is usually from 1 to 5 hours, preferably from 1 to 2 hours.

The isolation and purification are performed by employing a common scientific procedure such as extraction, concentration, distillation, crystallization, filtration, recrystallization, or various types of chromatography, however, a preferred procedure is filtration.
Synthesis of Carboxyl Group-Substituted Compound (4e)

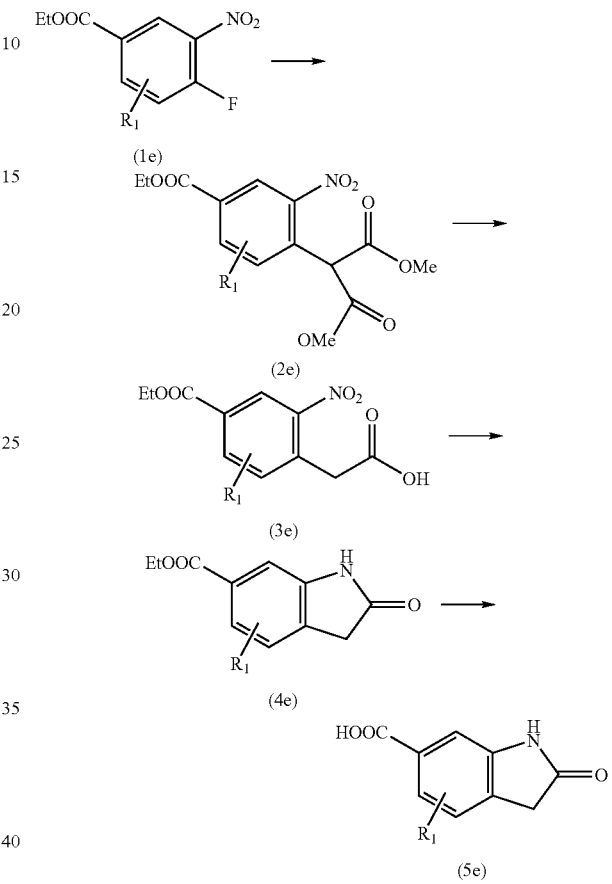

DMSO is added to sodium hydride, and dimethyl malonate is gradually added thereto while stirring. To the thus obtained solution, (1e) is added, followed by isolation and purification, whereby a dimethyl ester compound (2e) can be obtained. To this dimethyl ester compound (2e), a hydrochloric acid solution is added, followed by isolation and purification, whereby a methyl ester compound (3e) can be obtained. The carboxylic acid compound (3e) is reduced with palladium-carbon, followed by isolation and purification, whereby an oxindole ethyl ester compound (4e) can be obtained. After (4e) is dissolved in an ethanolic potassium hydroxide solution, an aqueous hydrochloric acid solution is further added thereto, followed by isolation and purification, whereby a carboxyl group-substituted compound (5e) can be obtained.

The reaction temperature is from 0 to 100° C., preferably from 20 to 50° C.

The isolation and purification can be performed by employing a common scientific procedure such as extraction, concentration, distillation, crystallization, filtration, recrystallization, or various types of chromatography.

Raw material compounds and various types of reagents in the production of the compound employed in the invention may form a salt, a hydrate or a solvate. Such raw material compounds and reagents are different depending on a starting raw material, a solvent to be used and the like, and are not particularly limited as long as they do not inhibit the reaction. It goes without saying that a solvent to be used is different depending on a starting raw material, a reagent and the like, and is particularly limited as long as it does not inhibit the reaction and dissolves a starting substance to some extent. When the compound employed in the invention is obtained in a free form, it can be converted into a form of a salt which may be formed by the compound, or a hydrate thereof according to a common procedure.

When the compound employed in the invention is obtained as a salt or a hydrate of the compound, the salt or the hydrate of the compound can be converted into a free form of the compound according to a common procedure.

Various isomers (for example, geometric isomers, optical isomers based on asymmetric carbons, rotation isomers, stereoisomers, tautomers, etc.) obtained for the compound employed in the invention can be purified and isolated using a common separation method, for example, recrystallization, a diastereomer salt method, an enzymolysis method, various types of chromatography (for example, thin layer chromatography, column chromatography, gas chromatography, etc.).

The compound employed in the invention has kinase inhibitory activity. The compound particularly has serine/threonine kinase inhibitory activity, and above all, particularly has Pim kinase inhibitory activity. Examples of the Pim kinase inhibitory activity include Pim-1 kinase inhibitory activity, Pim-2 kinase inhibitory activity and Pim-3 kinase inhibitory activity.

The compound employed in the invention has kinase inhibitory activity, and is useful as a kinase inhibitor, particularly as a Pim kinase inhibitor containing the compound or a pharmaceutically acceptable salt thereof as an active ingredient.

The compound employed in the invention has kinase inhibitory activity, and is effective as a preventive and/or therapeutic agent for a kinase-related disease, particularly a Pim kinase-related disease. Specific examples of the disease include cancer, apoptosis induction, potentiation of anticancer agent, overcoming of resistance to anticancer agent, or cell proliferation disorders, cardiac disturbance, myocardial infarction, arteriosclerosis, occlusive cardiovascular diseases, rheumatoid arthritis, diabetic retinopathy, age-related macular degeneration retinopathy, neurodegenerative diseases, autoimmune diseases, inflammatory diseases, diabetes and viral diseases. Particularly, the compound effectively functions as a preventive and/or therapeutic agent for cancer.

The compound employed in the invention can be an agent for inducing apoptosis, and is also useful as a preventive and/or therapeutic agent for a disease caused by inhibition of apoptosis, specifically, for example, an occlusive cardiovascular disease, arteriosclerosis, myocardial infarction or the like.

The method for inhibiting kinase activity of the invention can include: administering a pharmaceutically effective amount of the compound employed in the invention a patient with a kinase-related disease can be exemplified. Further, the method for preventing and/or treating a kinase-related disease of the invention includes administering a pharmaceutically effective amount of the compound employed in the invention to a patient with a kinase-related disease. Incidentally, preferred embodiments of the compound are as described above.

The uses according to the invention include use of the compound employed in the invention for producing a kinase inhibitor. Further, they also includes use of the compound employed in the invention for producing a preventive and/or therapeutic agent for a kinase-related disease.

When the compound employed in the invention is used in combination with an existing compound having an anticancer effect, for example, cisplatin, 5-fluorouracil, gemcitabine, doxorubicin (adriamycin) or the like, particularly, an anticancer effect is significantly potentiated.

Accordingly, another embodiment of the invention can include a combined therapeutic agent for cancer comprising a combination of the compound employed in the invention with a chemotherapeutic agent.

Such a combined therapeutic agent for cancer may be a compounding agent comprising a compound represented by any of the above-mentioned formulae or a compound represented by any of preferred embodiments thereof and a known compound having an anticancer effect (an anticancer compound), or a kit comprising an agent containing a compound represented by any of the above-mentioned formulae or a preferred embodiment thereof and an agent containing a known compound having an anticancer effect (a chemotherapeutic agent).

The compound employed in the invention can be administered as it is or after formulating it into a preparation together with a physiologically acceptable carrier such as an adjuvant for promotion of intake thereof. In the case where the compound is used for preventing and/or treating a kinase-related disease, it is preferred to use the compound which has been purified to a purity of preferably 90%, more preferably 95% or higher, further more preferably 98% or higher, most preferably 99% or higher.

The compound can be used, for example, orally as a tablet which may be coated with sugar if necessary, a capsule, an elixir, a microcapsule or the like, or in the form of an aerosolized inhalant, or parenterally in the form of an injectable preparation such as a sterile solution or suspension with water or a pharmaceutically acceptable liquid other than water.

For example, such a preparation can be produced by mixing the compound of the invention with a physiologically acceptable carrier, a flavoring agent, an excipient, a vehicle, an antiseptic, a stabilizer, a binder, or the like in a generally accepted unit dosage form as being required for the pharmaceutical manufacturing practice. The amount of the active ingredient in such a preparation is controlled such that an appropriate dose within a given range can be obtained. As an additive miscible with tablets, capsules and the like, for example, a binder such as gelatin, cornstarch, tragacanth or gum Arabic, an excipient such as crystalline cellulose, a swelling agent such as cornstarch, gelatin or alginic acid, a lubricant such as magnesium stearate, a sweetening agent such as sucrose, lactose or saccharin, a flavoring agent such as peppermint, akamono oil or cherry or the like is used. In the case where the unit dosage form is in the form of a capsule, a liquid carrier such as an oil or fat may further be used together with the material described above. The injectable preparation is prepared by dissolving, suspending or emulsifying a polypeptide of the invention in a sterile aqueous or oleaginous liquid to be commonly used for injectable preparations. As the aqueous liquid for injection, for example, physiological saline, an isotonic solution containing glucose and another auxiliary agent or the like is used. An appropriate solubilizing agent such as alcohol (for example, ethanol), a polyalcohol (for example, propylene glycol or polyethylene glycol), a nonionic surfactant (for example, polysorbate 80, HCO-50 (polyoxyethylene (50 mol) adduct of hydrogenated castor oil)) or the like may be used in combination. As the oleaginous liquid, for example, sesame oil, soybean oil or the like is used, and as a solubilizing agent, benzyl benzoate, benzyl alcohol or the like may be used in combination. Further, a buffer (for example, a phosphate buffer, a sodium acetate buffer, etc.), a soothing agent (for example, benzalkonium chloride, procaine hydrochloride, etc.), a stabilizer (for example, human serum albumin, polyethylene glycol, etc.), a preservative (for example, benzyl alcohol, phenol, etc.), an antioxidant, or the like may be added thereto. The prepared injection liquid is usually put into an appropriate ampule.

The thus obtained preparations are safe and low in toxicity, and therefore, they can be administered to, for example, warm-blooded animals (for example, humans, rats, mice, guinea pigs, rabbits, birds, sheep, swine, cattle, horses, cats, dogs, monkeys, chimpanzees, etc.) and can be used as a preventive and/or therapeutic agent for cancer, an apoptosis inducer or an anticancer agent potentiator, or can be used for preventing and/or treating a patient with a cell proliferation disorder, cardiac disturbance, a cardiovascular disease, myocardial infarction, arteriosclerosis, an occlusive cardiovascular disease, rheumatoid arthritis, diabetic retinopathy, age-related macular degeneration retinopathy, a neurodegenerative disease, an autoimmune disease, an inflammatory disease, diabetes or a viral disease.

The dose significantly varies depending on type of disease, degree of symptom, age, sex and sensitivity to drugs of patient and the like, however, administration is usually carried out in a dose of from about 0.03 to 1000 mg/day, preferably from 0.1 to 500 mg/day, more preferably from about 0.1 to 100 mg/day once a day or several times a day in divided portions. In the case of the injectable preparation, the dose is usually from about 1 µg/kg to 3000 µg/kg, preferably from about 3 µg/kg to 1000 µg/kg.

Incidentally, all of the prior art documents cited herein are incorporated herein by reference.

MODE FOR CARRYING OUT THE INVENTION

Figure 1A:
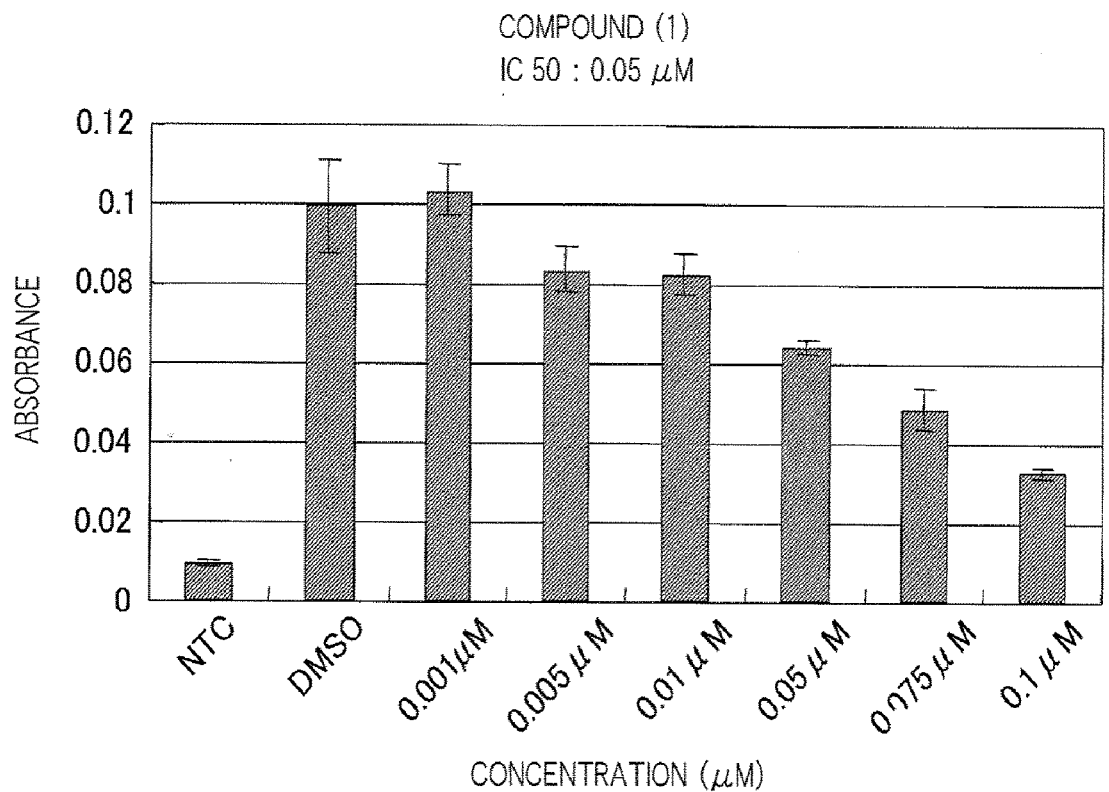
FIG. 1A It is a view showing the Pim-1 kinase inhibitory activity of a compound (1). The bar graph shows the concentration dependence of the Pim-1 kinase inhibitory activity of the compound (1); the horizontal axis indicates the concentration (µM) of the compound; and the vertical axis indicates the absorbance at a wavelength of 450 nm, which represents the Pim-1 kinase activity. The line graph is a view for performing calibration of IC50 of the Pim-1 kinase inhibitory activity of the compound (1); the horizontal axis indicates the concentration (µM) of the compound; and the vertical axis indicates the inhibition ratio (%) of the Pim-1 kinase activity when the value obtained for a DMSO solvent control is taken to be 100%.
Figure 1A:
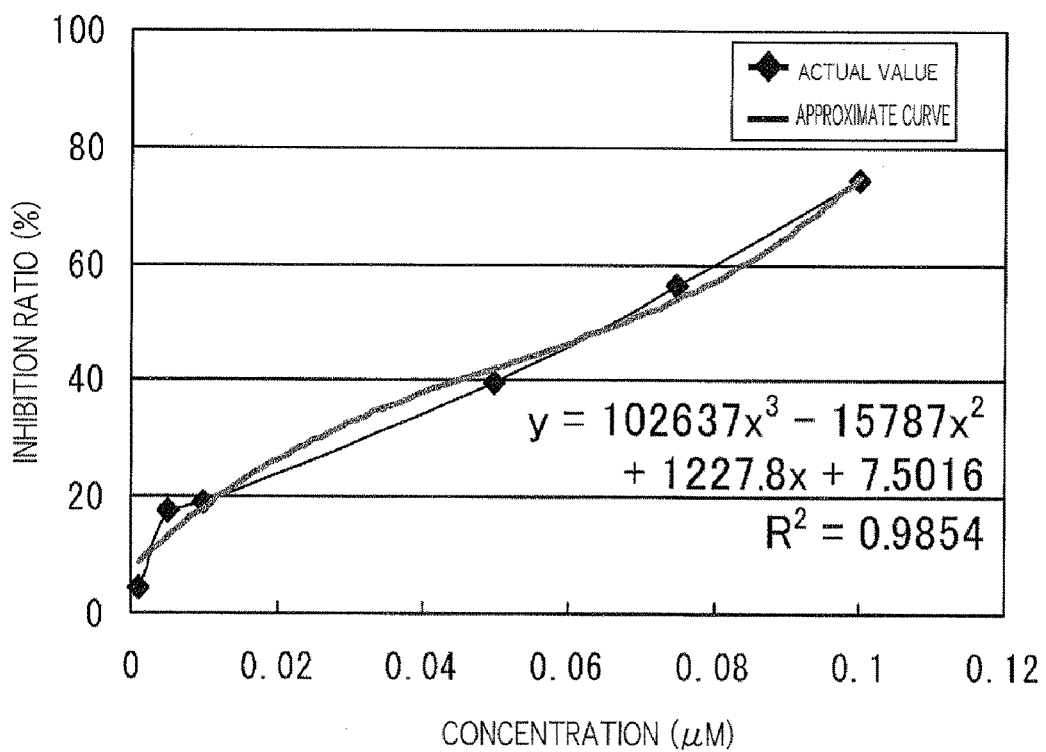
Figure 1B:
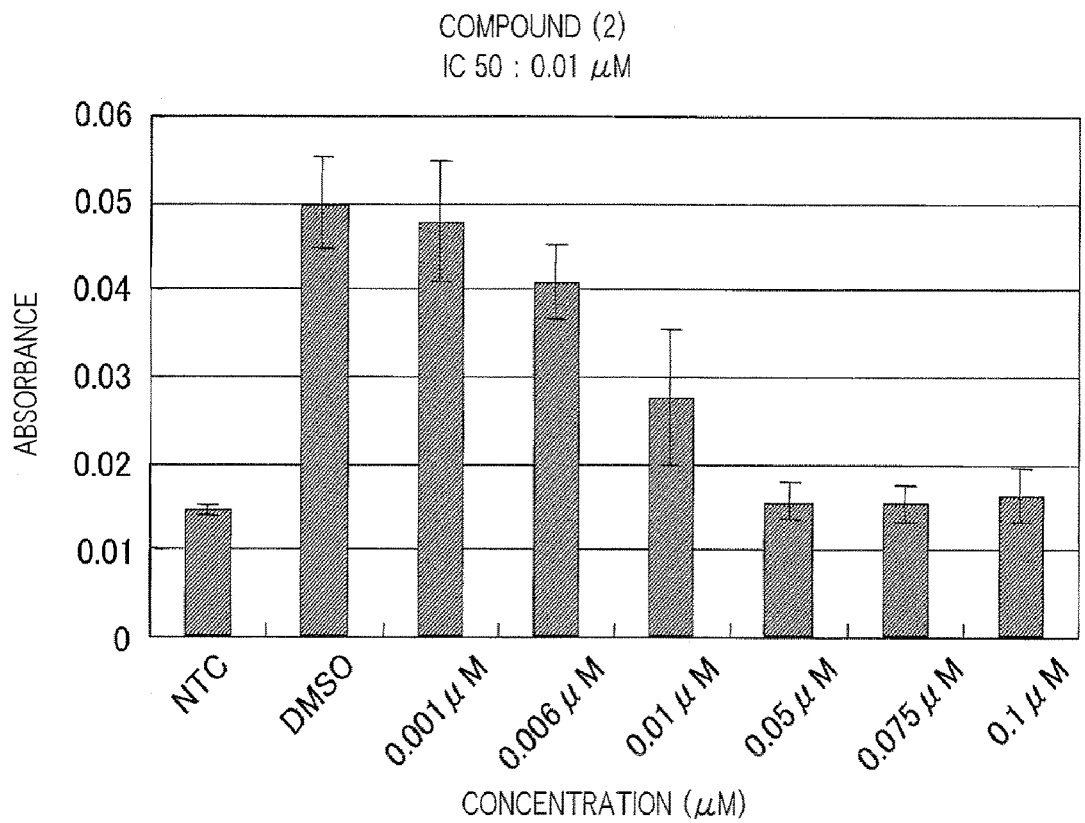
FIG. 1B It is a view showing the Pim-1 kinase inhibitory activity of a compound (2). The bar graph shows the concentration dependence of the Pim-1 kinase inhibitory activity of the compound (2); the horizontal axis indicates the concentration (µM) of the compound; and the vertical axis indicates the absorbance at a wavelength of 450 nm, which represents the Pim-1 kinase activity. The line graph is a view for performing calibration of IC50 of the Pim-1 kinase inhibitory activity of the compound (2); the horizontal axis indicates the concentration (µM) of the compound; and the vertical axis indicates the inhibition ratio (%) of the Pim-1 kinase activity when the value obtained for a DMSO solvent control is taken to be 100%.
Figure 1B:
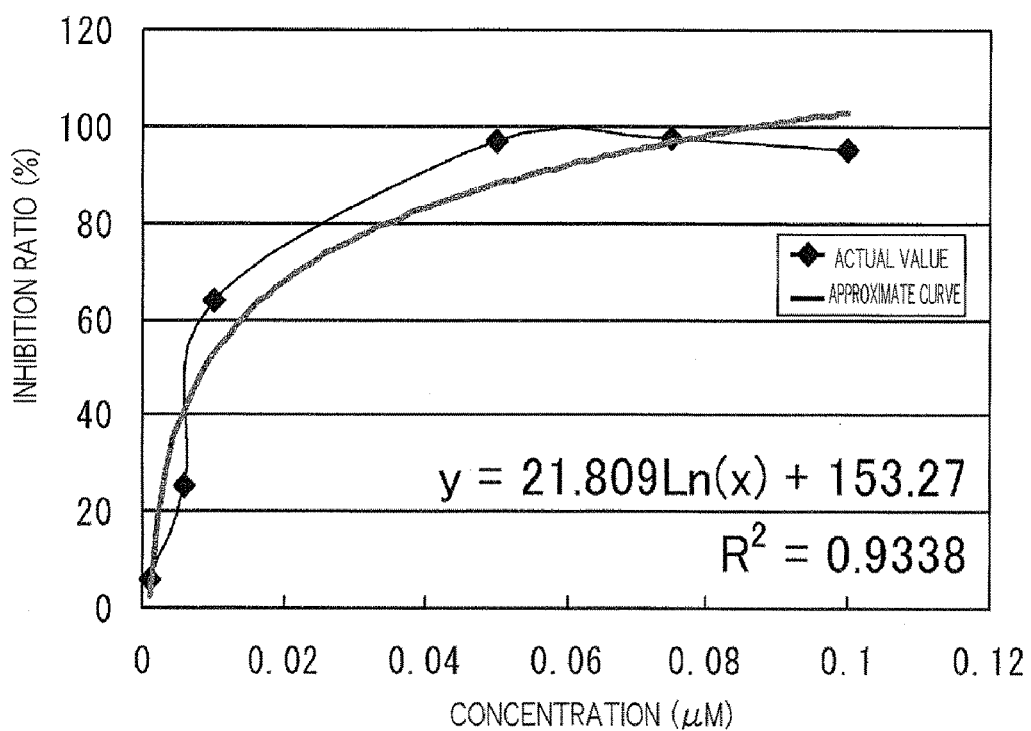
Figure 1C:
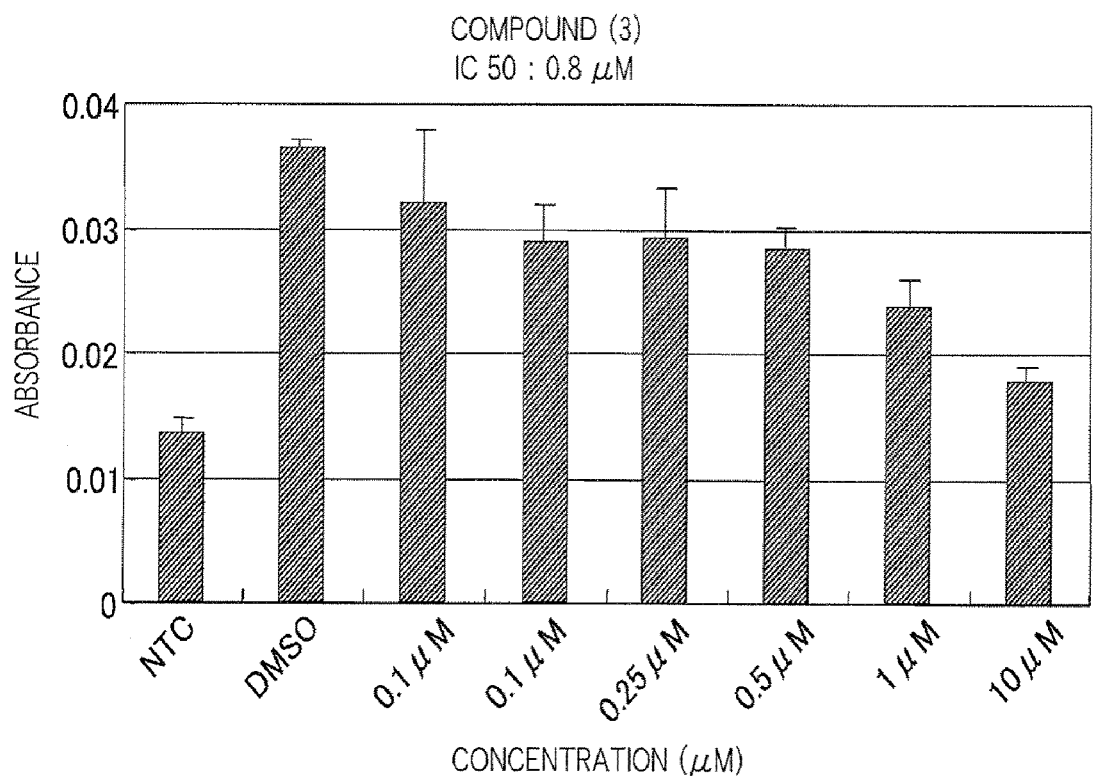
FIG. 1C It is a view showing the Pim-1 kinase inhibitory activity of a compound (3). The bar graph shows the concentration dependence of the Pim-1 kinase inhibitory activity of the compound (3); the horizontal axis indicates the concentration (µM) of the compound; and the vertical axis indicates the absorbance at a wavelength of 450 nm, which represents the Pim-1 kinase activity. The line graph is a view for performing calibration of IC50 of the Pim-1 kinase inhibitory activity of the compound (3); the horizontal axis indicates the concentration (µM) of the compound; and the vertical axis indicates the inhibition ratio (%) of the Pim-1 kinase activity when the value obtained for a DMSO solvent control is taken to be 100%.
Figure 1C:
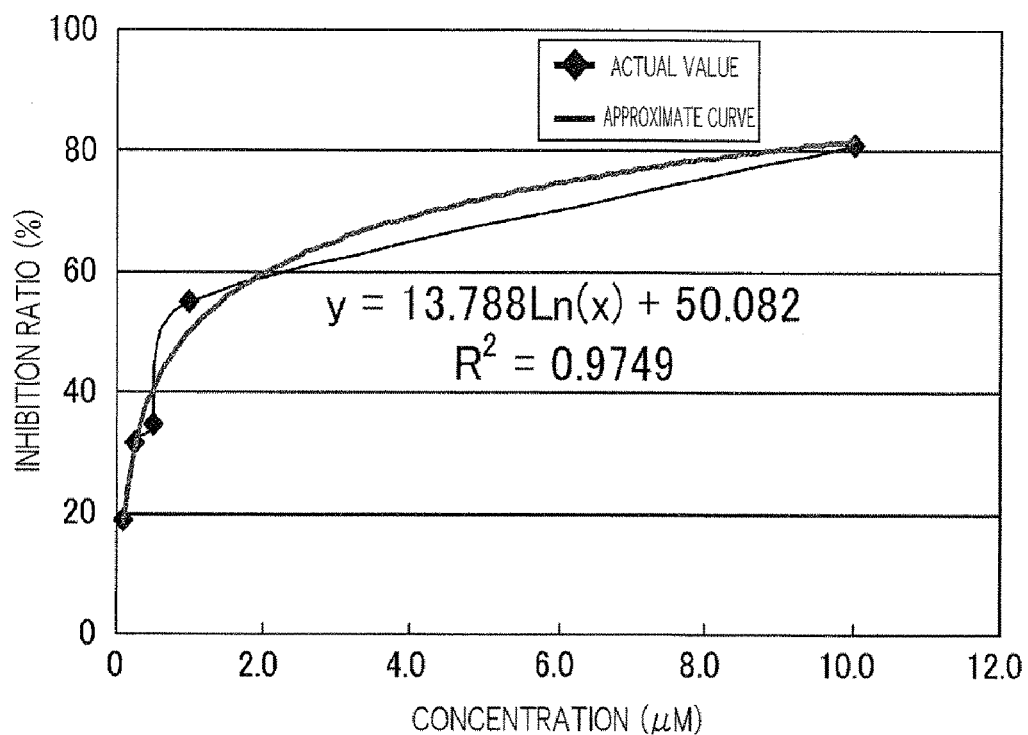
Figure 1D:
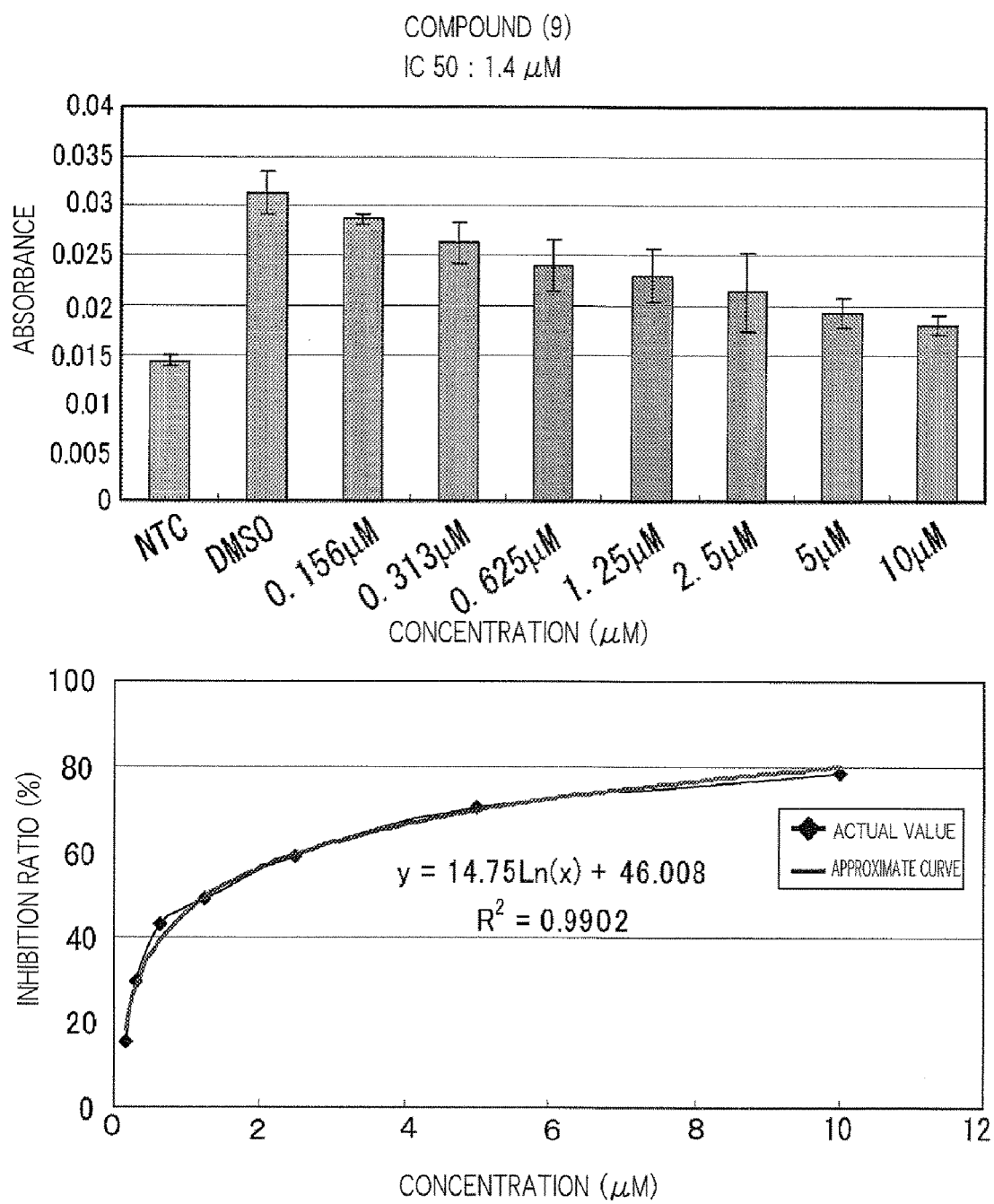
FIG. 1D It is a view showing the Pim-1 kinase inhibitory activity of a compound (9). The bar graph shows the concentration dependence of the Pim-1 kinase inhibitory activity of the compound (9); the horizontal axis indicates the concentration (µM) of the compound; and the vertical axis indicates the absorbance at a wavelength of 450 nm, which represents the Pim-1 kinase activity. The line graph is a view for performing calibration of IC50 of the Pim-1 kinase inhibitory activity of the compound (9); the horizontal axis indicates the concentration (µM) of the compound; and the vertical axis indicates the inhibition ratio (%) of the Pim-1 kinase activity when the value obtained for a DMSO solvent control is taken to be 100%.
Figure 1E:
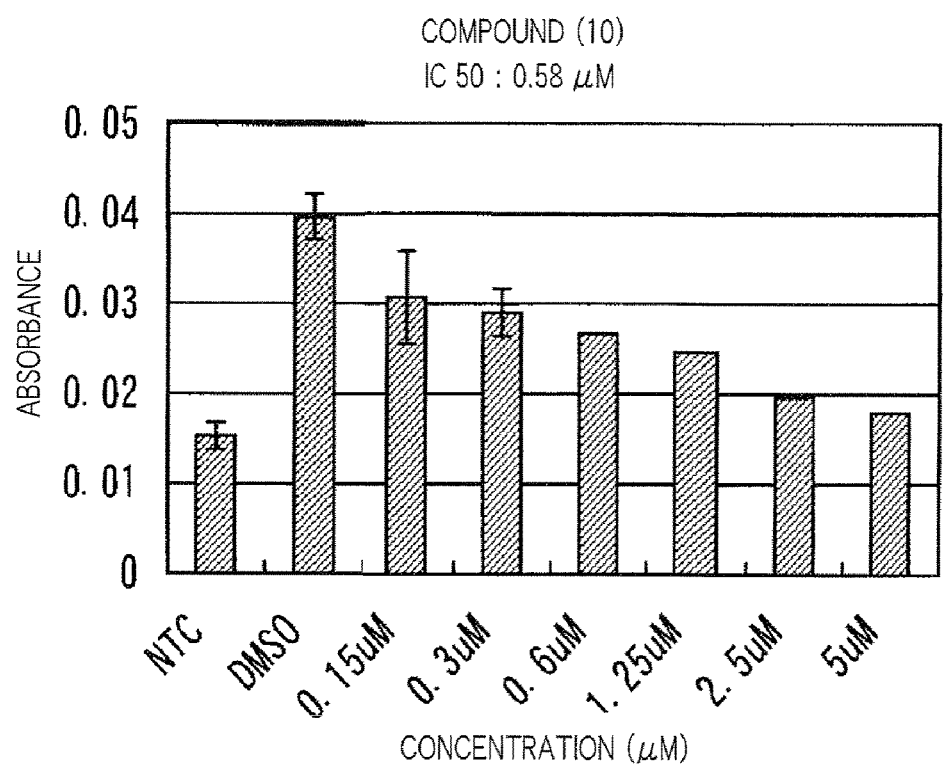
FIG. 1E It is a view showing the Pim-1 kinase inhibitory activity of a compound (10). The bar graph shows the concentration dependence of the Pim-1 kinase inhibitory activity of the compound (10); the horizontal axis indicates the concentration (µM) of the compound; and the vertical axis indicates the absorbance at a wavelength of 450 nm, which represents the Pim-1 kinase activity. The line graph is a view for performing calibration of IC50 of the Pim-1 kinase inhibitory activity of the compound (10); the horizontal axis indicates the concentration (µM) of the compound; and the vertical axis indicates the inhibition ratio (%) of the Pim-1 kinase activity when the value obtained for a DMSO solvent control is taken to be 100%.
Figure 1E:
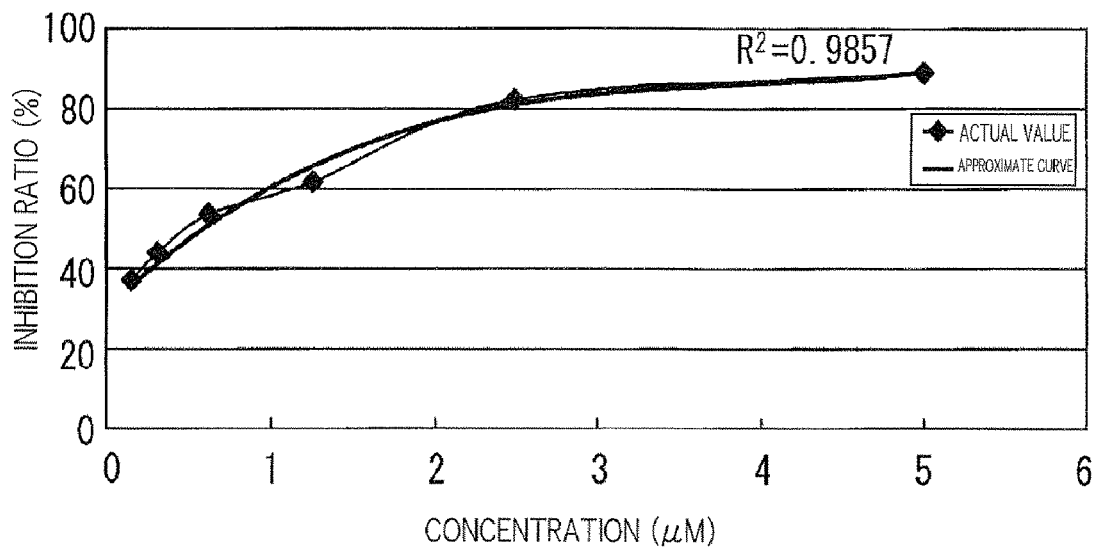
Figure 1F:
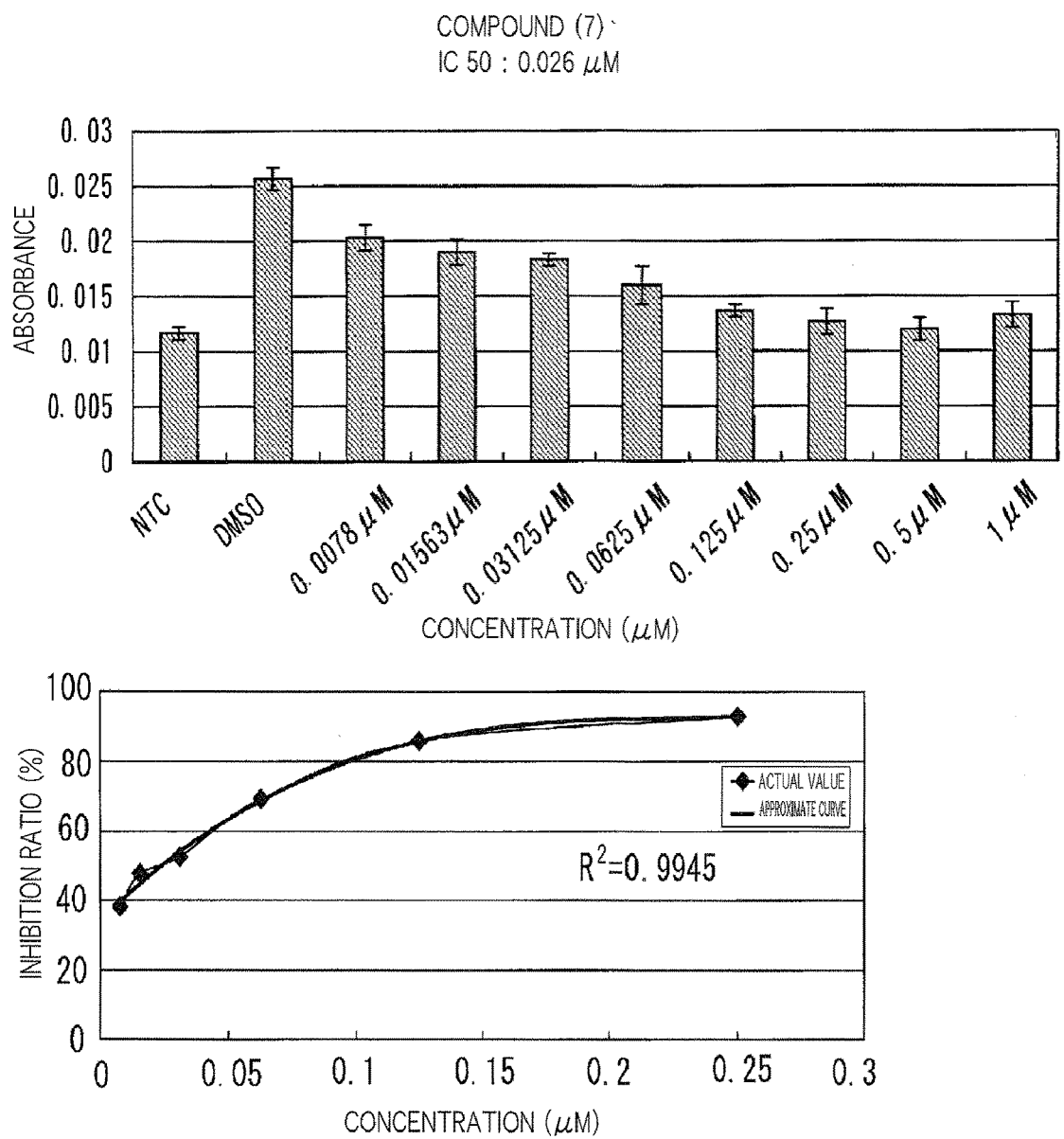
FIG. 1F It is a view showing the Pim-1 kinase inhibitory activity of a compound (7). The bar graph shows the concentration dependence of the Pim-1 kinase inhibitory activity of the compound (7); the horizontal axis indicates the concentration (µM) of the compound; and the vertical axis indicates the absorbance at a wavelength of 450 nm, which represents the Pim-1 kinase activity. The line graph is a view for performing calibration of IC50 of the Pim-1 kinase inhibitory activity of the compound (7); the horizontal axis indicates the concentration (µM) of the compound; and the vertical axis indicates the inhibition ratio (%) of the Pim-1 kinase activity when the value obtained for a DMSO solvent control is taken to be 100%.
Figure 2A:
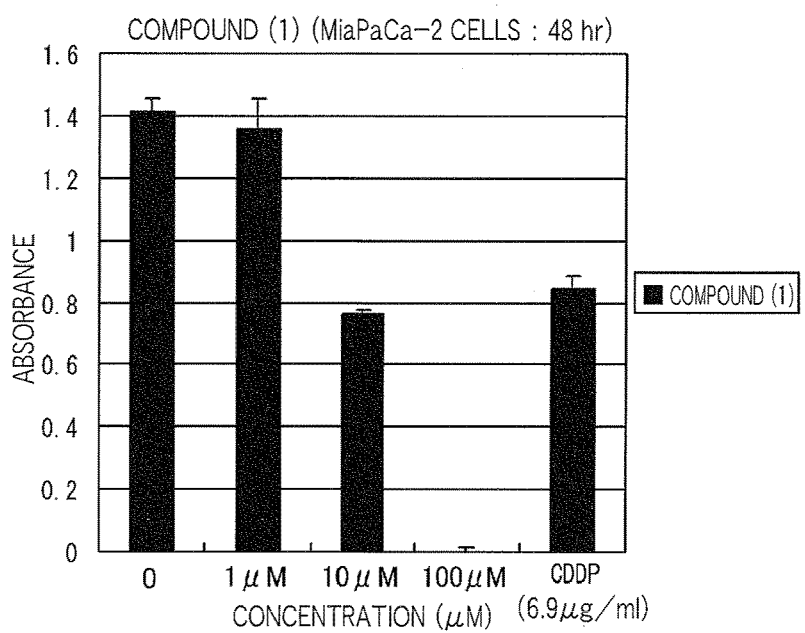
FIG. 2A It is a view showing the cytotoxicity of the compound (1) to a pancreatic cancer cell line (MiaPaCa-2); the horizontal axis indicates the concentration (µM) of the compound; and the vertical axis indicates the absorbance at a wavelength of 490 nm, which shows the viable cell count and represents the cytotoxic activity. Incidentally, CDDP in the drawing stands for cisplatin to be compared.
Figure 2B:
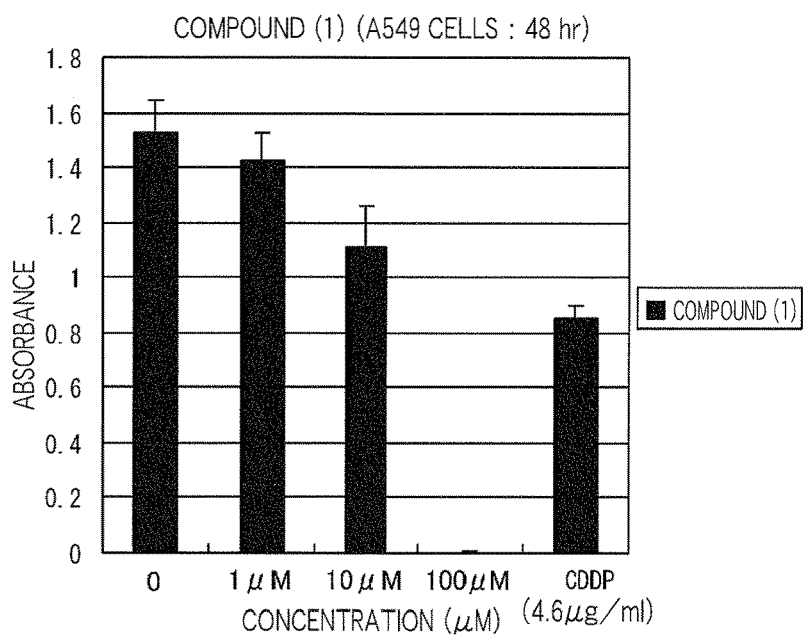
FIG. 2B It is a view showing the cytotoxicity of the compound (1) to a lung cancer cell line (A549); the horizontal axis indicates the concentration (µM) of the compound; and the vertical axis indicates the absorbance at a wavelength of 490 nm, which shows the viable cell count and represents the cytotoxic activity. Incidentally, CDDP in the drawing stands for cisplatin to be compared.
Figure 2C:
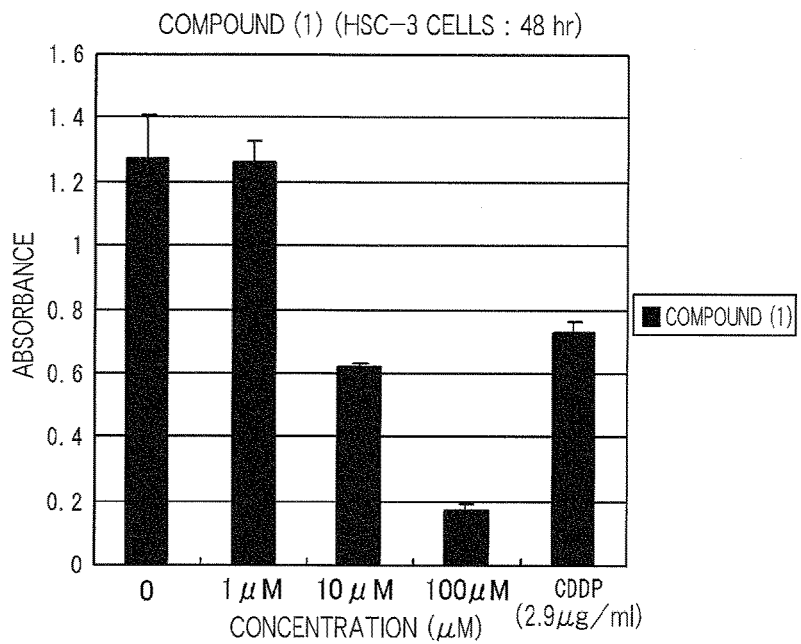
FIG. 2C It is a view showing the cytotoxicity of the compound (1) to an oral squamous cell carcinoma cell line (HSC-3); the horizontal axis indicates the concentration (µM) of the compound; and the vertical axis indicates the absorbance at a wavelength of 490 nm, which shows the viable cell count and represents the cytotoxic activity. Incidentally, CDDP in the drawing stands for cisplatin to be compared.
Figure 2D:
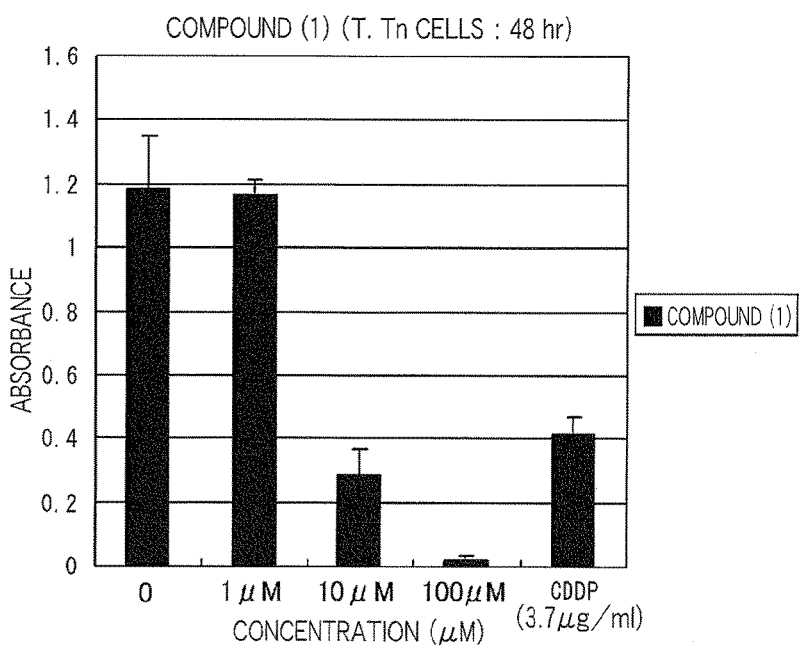
FIG. 2D It is a view showing the cytotoxicity of the compound (1) to an esophageal squamous cell carcinoma cell line (T.Tn); the horizontal axis indicates the concentration (μM) of the compound; and the vertical axis indicates the absorbance at a wavelength of 490 nm, which shows the viable cell count and represents the cytotoxic activity. Incidentally, CDDP in the drawing stands for cisplatin to be compared.
Figure 2E:
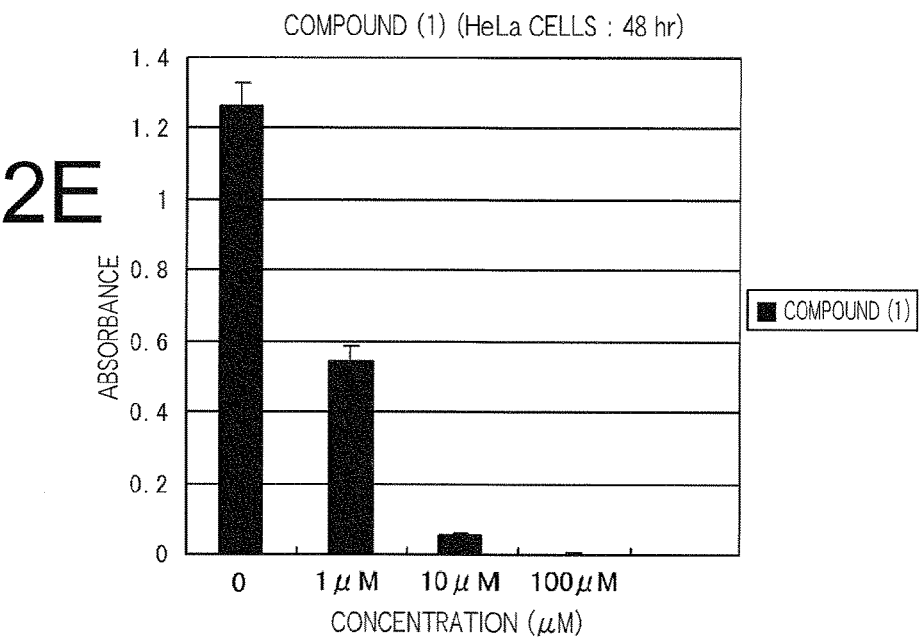
FIG. 2E It is a view showing the cytotoxicity of the compound (1) to a uterine cancer cell line (HeLa); the horizontal axis indicates the concentration (μM) of the compound; and the vertical axis indicates the absorbance at a wavelength of 490 nm, which shows the viable cell count and represents the cytotoxic activity.
Figure 2F:
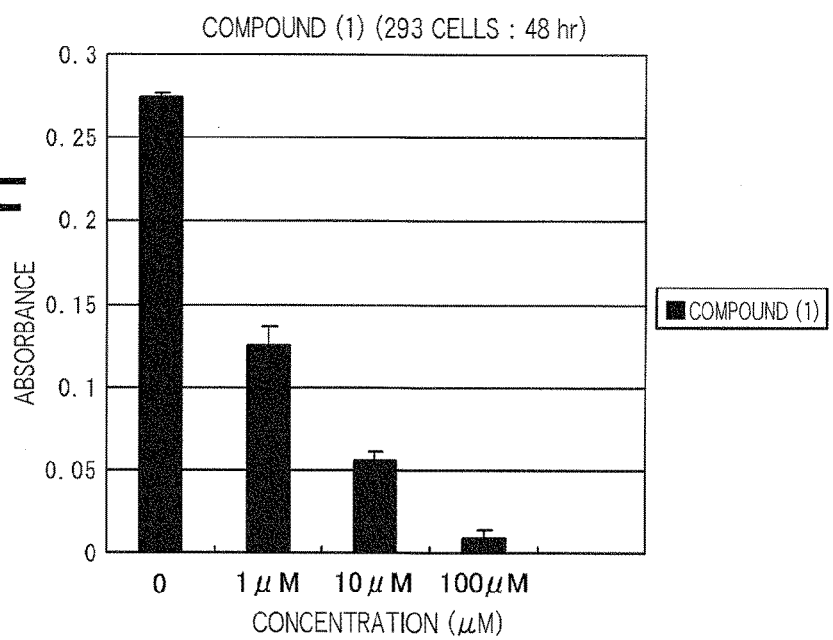
FIG. 2F It is a view showing the cytotoxicity of the compound (1) to a normal renal cell line (293); the horizontal axis indicates the concentration (μM) of the compound; and the vertical axis indicates the absorbance at a wavelength of 490 nm, which shows the viable cell count and represents the cytotoxic activity.

Hereinafter, the invention will be more specifically described by showing Examples, without being limitative thereto.

The raw material compounds such as oxindole and diformylfuran to be used below are known, and for example, oxindole (O02721, Tokyo Chemical Industry Co., Ltd.) and diformylfuran (D2408, Tokyo Chemical Industry Co., Ltd.) can be easily obtained as commercially available products.

EXAMPLE 1

(3E)-3[(5-((E)-(2-oxoindolin-3-ylidene)methyl)furan-2-yl)methylene]indoline-2-one (1)

Oxindole (1 equivalent), diformylfuran (0.5 equivalent) and piperidine (0.2 equivalent) were dissolved in ethanol such that 1 mL of ethanol was used per 1 μmol of the total amount of the compounds, and the resulting mixture was stirred at room temperature for 12 hours. After completion of the reaction, the resulting precipitate was collected by filtration, washed with cooled ethanol several times and dried, whereby a target compound was obtained in a yield of 45%.

$^1$H-NMR (d$_6$-DMSO, 400 Mz): 13.20 (s, 1H), 13.18 (s, 1H), 11.01 (d, J=7.84 Hz, 1H), 10.98 (d, J=3.92 Hz), 10.43 (d, J=7.84 Hz, 1H), 10.10 (d, J=7.35 Hz, 1H), 10.08 (s, 1H), 9.96 (d, J=3.92 Hz, 1H), 9.82 (s, 1H), 9.80-9.65 (m, 2H), 9.52 (t, J=7.84 Hz, 1H—), 9.37 (t, J=7.84 Hz, 1H), 9.11 (t, J=7.84 Hz, 1H), MS m/z: 355 (M)$^+$

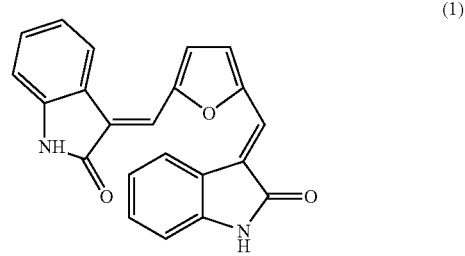

(1)

EXAMPLE 2

(3E)-1-acetyl-3-[((5E)-((1-acetyl-2-oxoindolin-3-ylidene)methyl)furan-2-yl)methylene]indolin-2-one (2)

Oxindole (1 equivalent) was dissolved in acetic anhydride and the resulting mixture was heated under reflux for 3 days. After cooling, the reaction mixture was poured into ice water. The resulting precipitate was collected by filtration, washed with water and dried, whereby 1-acetyloxindole was obtained. From the thus obtained 1-acetyloxindole and diformylfuran, a target compound was obtained in the same manner as in Example 1.

$^1$H-NMR (d$_6$-DMSO, 400 Mz): 11.05 (d, J=7.84 Hz, 1H), 11.00 (d, J=3.92 Hz), 10.46 (d, J=7.84 Hz, 1H), 10.13 (d, J=7.35 Hz, 1H), 10.04 (s, 1H), 9.94 (d, J=3.92 Hz, 1H), 9.80 (s, 1H), 9.78-9.63 (m, 2H), 9.43 (t, J=7.84 Hz, 1H—), 9.30 (t, J=7.84 Hz, 1H), 9.08 (t, J=7.84 Hz, 1H), 2.38 (s, 3H), 2.36 (s, 3H). MS m/z: 438 (M)$^+$

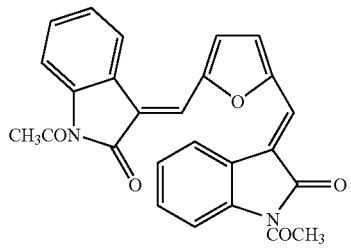

(2)

EXAMPLE 3

(3E)-3-((5-((E)-(1-acetyl-2-oxoindolin-3-ylidene)methyl)furan-2-yl)methylene)indolin-2-one (3)

Diformylfuran (1 equivalent) was dissolved in ethanol, and a solution obtained by dissolving oxindole (0.5 equivalent) and piperidine (0.1 equivalent) in ethanol was gradually added thereto. After completion of the addition, the resulting mixture was stirred at room temperature for 2 hours. After completion of the reaction, the resulting precipitate was removed by filtration. To the filtrate, acetone was added and the resulting solution was acidified with a 1 N hydrochloric acid solution and evaporated to dryness under reduced pressure, whereby 5-((E)-(indolin-3-ylidene)methyl)furan-2-carbaldehyde was obtained (yield: 31%). Subsequently, the thus obtained 5-((E)-(indolin-3-ylidene)methyl)furan-2-carbaldehyde (1.2 equivalents), 1-acetyloxindole (1 equivalent) and piperidine (0.1 equivalent) were dissolved in ethanol and the resulting mixture was stirred at room temperature for 12 hours. After completion of the reaction, the resulting precipitate was collected by filtration, washed with cooled ethanol and dried, whereby a target compound was obtained.

$^1$H-NMR (d$_6$-DMSO, 400 Mz): 10.68 (d, J=7.84 Hz, 1H), 10.62 (d, J=3.92 Hz, 1H), 10.45 (s, 1H), 8.51 (m, 1H), 8.02 (t, J=8.55 Hz, 1H), 8.01 (s, 1H), 7.52 (s, 1H), 7.05 (d, J=3.66 Hz, 1H), 6.88 (d, J=8.55 Hz, 1H), 6.83 (t, J=7.08 Hz), 6.61 (t, J=7.57, 1H), 6.51 (t, J=7.57 Hz, 1H), 2.67 (s, 3H), MS m/z: 396 (M)$^+$

EXAMPLE 4

(3E)-3-[(5-(E)-(5-carboxy-2-oxoindolin-3-ylidene)methyl)furan-2-yl)methylene]-2-oxoindolin-5-carboxylic acid (4)

Under ice-cooling, aluminum chloride (anhydride) (3.5 equivalents) was suspended in methylene chloride, and oxindole (1 equivalent) was added to this solution while stirring. To this solution, chioroacetyl chloride (2 equivalents) was gradually added dropwise, and after generation of hydrogen chloride gas was stopped, the resulting mixture was stirred for about 10 minutes. Thereafter, the reaction mixture was warmed to 40 to 50° C. and stirred for 2 hours. After cooling, the reaction mixture was poured into ice water and the resulting precipitate was collected by filtration, washed with water and dried, whereby 5-chloroacetylindolin-2-one was obtained. 5-chloroacetylindolin-2-one was dissolved in pyridine and the resulting mixture was heated and stirred at 80 to 90° C. for 3 hours. After cooling, the resulting precipitate was collected by filtration, washed with ethanol several times and dissolved in 2.5 N sodium hydroxide, and the resulting solution was stirred at 70 to 75° C. After cooling, the reaction mixture was acidified with hydrochloric acid and the resulting precipitate was collected by filtration, washed with water and dried, whereby 5-carboxyindolin-2-one was obtained. From the thus obtained 5-carboxyindolin-2-one and diformylfuran, a target compound was obtained in the same manner as in Example 1.

$^1$H-NMR (d$_6$-DMSO, 400 Mz): 12.30 (s, br, 2H), 11.15 (d,J=7.84 Hz, 1H),11.02 (d, J=3.92 Hz), 10.46 (d, J=7.84 Hz, 1H), 10.13 (d, J=7.35 Hz, 1H), 10.04 (s, 1H), 9.98 (d, J=3.92 Hz, 1H), 9.80 (s, 1H), 9.88-9.73 (m, 2H), 9.53 (t, J=7.84 Hz, 1H), MS m/z: 442(M)$^+$

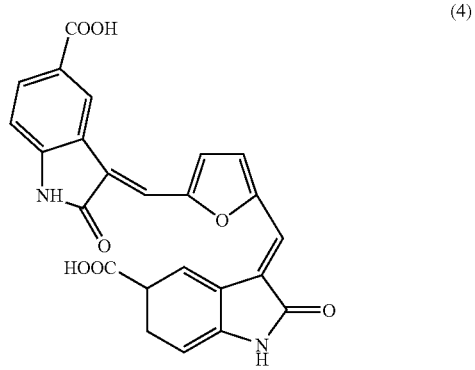

(4)

EXAMPLE 5

(3E)-3-[(5-((E)-(5-carboxy-2-oxoindolin-3-ylidene)methyl)furan-2-yl)methylene]-2-oxoindolin-5-carboxylic acid disodium salt (8)

The compound (4) (1 equivalent) and sodium hydroxide (2 equivalents) were dissolved in ethanol, and the resulting precipitate was collected by filtration, washed with ethanol several times and dried, whereby a sodium salt of the compound (4) was obtained.

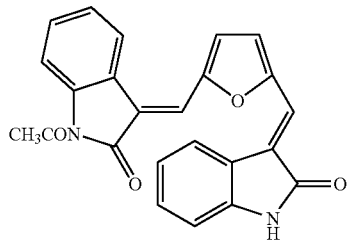

(3)

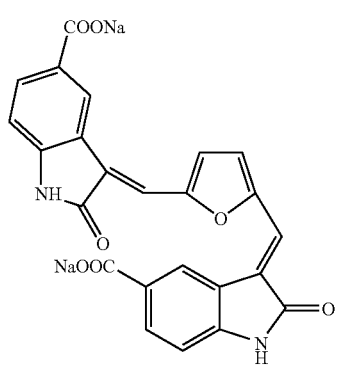

(8)

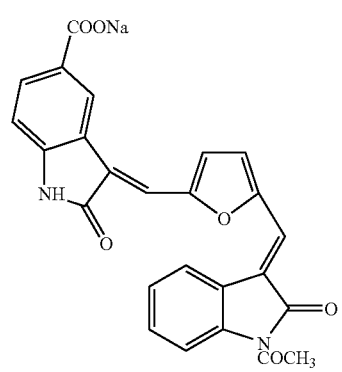

(9)

EXAMPLE 6

(3E)-3-((5-((E)-(1-acetyl-2-oxoindolin-3-ylidene)methyl)furan-2-yl)methylene)-2-oxoindoline-5-carboxylic acid (5)

5-carboxylndolin-2-one (1 equivalent), 3-((5-formylfuran-2-yl)methylene)-N-acetyl-2-oxoindoline (1.2 equivalents) and piperidine (0.2 equivalent) were dissolved in ethanol such that 1 mL of ethanol was used per 1 μmol of the total amount of the compounds, and the resulting mixture was stirred at room temperature for 2 hours. After completion of the reaction, the resulting precipitate was collected by filtration, washed with cooled ethanol several times and dried, whereby a target compound was obtained.

$^1$H-NMR ($d_6$-DMSO, 400 Hz): 9.41 (s, 1H), 9.39 (s, 1H), 8.42 (d, J=3.91 Hz, 1H), 8.32 (d, J=3.91 Hz, 1H), 8.07 (s, 1H), 7.98 (s, 1H), 7.92 (d, J=8.05 Hz, 1H), 7.82 (d, J=8.05 Hz, 1H), 7.60 (s, 1H), 7.55 (dd, J=8.21 Hz, 1.72 Hz, 1H), 7.36 (d, J=7.22 Hz, 1H), 7.26 (d, J=7.22 Hz, 1H), 6.87 (m, 1H), 2.66 (s, 3H), MS m/z: 440 (M)$^+$

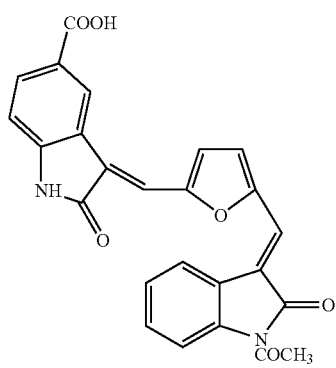

(5)

EXAMPLE 7

(3E)-3-((5-((E)-(1-acetyl-2-oxoindolin-3-ylidene)methyl)furan-2-yl)methylene)-2-oxoindoline-5-carboxylic acid sodium salt (9)

The compound (5) (1 equivalent) and sodium hydroxide (1 equivalent) were dissolved in ethanol, and the resulting precipitate was collected by filtration, washed with ethanol several times and dried, whereby a sodium salt (9) of the compound (5) was obtained.

EXAMPLE 8

(3E)-3-((5-((E)-(1-acetyl-2-oxoindolin-3-ylidene)methyl)furan-2-yl)methylene)-2-oxoindoline-6-carboxylic acid (6)

1. 4-fluoro-3-nitrobenzoic acid (1 equivalent) was dissolved in ethanol (5.3 equivalents), and concentrated sulfuric acid (0.25 equivalent) was added thereto, and the resulting mixture was heated under reflux for 5 hours. After cooling the reaction mixture, the reaction mixture was concentrated under reduced pressure until the volume was reduced to about half the initial value. The resulting mixture was then neutralized by adding sodium carbonate and was subjected to extraction with ether three times. The obtained extracted liquid was washed with saturated brine and then with water, and the ether layer was dried over anhydrous sodium sulfate. The resulting layer was then evaporated to dryness under reduced pressure, whereby ethyl 4-fluoro-3-nitrobenzoate was obtained.

2. 30 mL of anhydrous dimethyl sulfoxide was added to 0.98 g of sodium hydride defatted with hexane, and to the resulting solution, 2.98 g of dimethyl malonate was gradually added at room temperature while stirring. After completion of the dropwise addition, the resulting mixture was stirred at 100° C. for 1 hour. This mixture was cooled to room temperature, and 3 g (14 mmol) of ethyl 4-fluoro-3-nitrobenzoate was added thereto, and the resulting mixture was stirred at room temperature for 30 minutes and then further stirred at 100° C. for 1 hour. After the reaction mixture was cooled, saturated ammonium chloride was added thereto, and the resulting mixture was subjected to extraction with ethyl acetate. The obtained ethyl acetate layer was washed sequentially with saturated brine and water, dried over anhydrous sodium sulfate and then evaporated to dryness under reduced pressure, whereby ethyl 4-(di(methoxycarbonyl)methyl)-3-nitrobenzoate was obtained.

3. To 5.58 g of the thus obtained ethyl 4-(di(methoxycarbonyl)methyl)-3-nitrobenzoate, 9 mL of a 6 N hydrochloric acid solution was added and the resulting mixture was heated under reflux for 12 hours. After the reaction mixture was cooled, water was added thereto, and the resulting precipitate was removed by filtration, and the filtrate was subjected to extraction with ether. The obtained ether layer was washed with water, dried over anhydrous sodium sulfate and then evaporated to dryness under reduced pressure, whereby ethyl 4-(carboxylmethyl)-3-nitrobenzoate was obtained.

4. 4 g (15.8 mmol) of the thus obtained ethyl 4-(carboxymethyl)-3-nitrobenzoate and 0.45 g of 10% palladium-carbon were suspended in 15 mL of acetic acid, and the resulting mixture was stirred at room temperature in a hydrogen gas atmosphere for 23 hours. After completion of the reaction, water was added to the reaction mixture and the mixture was filtered to remove insoluble matter, and the filtrate was subjected to extraction with chloroform. The obtained chloroform layer was evaporated to dryness under reduced pressure, and water was added to the residue. Precipitated ethyl 2-oxoindoline-6-carboxylate was then obtained by filtration.

5. 300 mg of the thus obtained ethyl 2-oxoindoline-6-carboxylate was dissolved in 4 mL of an ethanolic potassium hydroxide solution, and the resulting mixture was stirred at 100° C. for 6 hours. The reaction mixture was cooled to room temperature, and 1 mL of a 6 N aqueous hydrochloric acid solution was added to acidify the reaction mixture, which was then heated again at 100° C. for minutes. The reaction mixture was cooled, and the precipitated 2-oxoindoline-6-carboxylic acid was collected by filtration.

6. N-acetyloxindole (1 equivalent), 5-hydroxymethyl-2-furaldehyde (0.5 equivalent) and piperidine (0.2 equivalent) were dissolved in ethanol such that 1 mL of ethanol was used per 1 μmol of the total amount of the compounds, and the resulting mixture was stirred at room temperature for 12 hours. After completion of the reaction, the resulting precipitate was collected by filtration, washed with cooled ethanol several times and dried, whereby 3-((5-(hydroxymethyl)furan-2-yl) methylene)-N-acetyl-2-oxoindoline was obtained.

7. The thus obtained 3-((5-(hydroxymethyl)furan-2-yl) methylene)-N-acetyl-2-oxoindoline (1 equivalent) and pyridinium chlorochromate (1.5 equivalents) were dissolved in methylene chloride and the resulting mixture was stirred at room temperature for 2 hours. After completion of the reaction, the reaction mixture was evaporated to dryness under reduced pressure, and to the residue, ethyl acetate was added. Insoluble matter was then removed by Celite filtration, and the filtrate was evaporated to dryness under reduced pressure, whereby a target compound was obtained.

8. 2-oxoindoline-6-carboxylic acid (1 equivalent), 3-((5-(formylfuran-2-yl)methylene)-N-acetyl-2-oxoindoline (1.2 equivalents) and piperidine (0.2 equivalent) were dissolved in ethanol such that 1 mL of ethanol was used per 1 μmol of the total amount of the compounds, and the resulting mixture was stirred at room temperature for 2 hours. After completion of the reaction, the resulting precipitate was collected by filtration, washed with cooled ethanol several times and dried, whereby (3E)-3-((5-((E)-(1-acetyl-2-oxoindolin-3-ylidene) methyl)furan-2-yl)methylene)-2-oxoindoline-6-carboxylic acid (6) was obtained.

$^1$H-NMR (d$_6$-DMSO, 400 Mz): 10.72 (s, br, 1H), 8.77 (s, 1H), 8.40 (d, J=3.91 Hz, 1H), 8.25 (m, 1H), 8.03 (s, 1H), 8.17 (t, J=7.81 Hz, 1H), 7.90 (s, 1H), 7.71 (s, 1H), 7.65 (d, J=3.91 Hz, 1H), 7.63 (d, J=7.80 Hz, 1H), 7.60 (d, J=7.80 Hz, 1H), 7.11 (d, J=7.80 Hz, 1H), 6.88 (t, J=7.81 Hz, 1H), 2.66 (s, 3H), MS m/z: 440 (M)$^+$

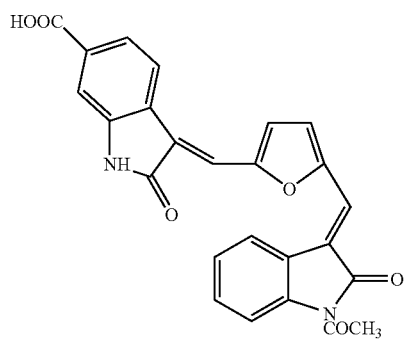

(6)

EXAMPLE 9

(3E)-3-((5-((E)-(1-acetyl-2-oxoindolin-3-ylidene) methyl)furan-2-yl)methylene)-2-oxoindoline-6-carboxylic acid sodium salt (10)

The compound (6) (1 equivalent) and sodium hydroxide (1 equivalent) were dissolved in ethanol, and the resulting precipitate was collected by filtration, washed with ethanol several times and dried, whereby a sodium salt (10) of the compound (6) was obtained.

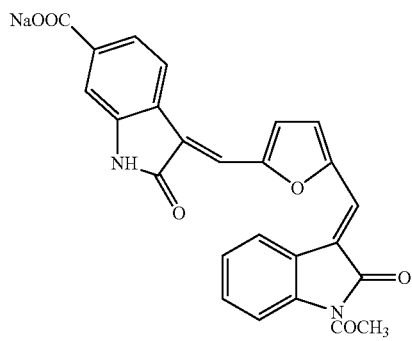

(10)

EXAMPLE 10

(3E)-1-butyryl-3-[((5E)-((1-butyryl-2-oxoindolin-3-ylidene)methyl)furan-2-yl)methylene]indolin-2-one (7)

Oxindole (7.56 mmol) was dissolved in butyric anhydride (11.39 mmol), and the resulting mixture was heated and stirred at 120° C. for 24 hours. After cooling, the reaction mixture was poured into ice water, and the resulting precipitate was collected by filtration, washed with water and dried, whereby 1-butyrylindolin-2-one was obtained.

The thus obtained 1-butyrylindolin-2-one (1 equivalent), diformylfuran (0.5 equivalent) and piperidine (0.2 equivalent) were dissolved in ethanol such that 1 mL of ethanol was used per 1 μmol of the total amount of the compounds, and the resulting mixture was stirred at room temperature for 12 hours. After completion of the reaction, the resulting precipitate was collected by filtration, washed with cooled ethanol several times and dried, whereby a target compound was obtained.

¹H-NMR (d₆-DMSO, 400 Mz): 11.02 (d, J=7.84 Hz, 1H), 10.98 (d, J=3.92 Hz), 10.36 (d, J=7.84 Hz, 1H), 10.23 (d, J=7.35 Hz, 1H), 9.98 (s, 1H), 9.90 (d, J=3.92 Hz, 1H), 9.76 (s, 1H), 9.76-9.62 (m, 2H), 9.41 (t, J=7.84 Hz, 1H—), 9.27 (t, J=7.84 Hz, 1H), 9.07 (t, J=7.84 Hz, 1H), 2.23 (m, 4H), 1.82 (m, 4H), 1.02 (m, 6H), MS m/z: 494 (M)⁺

(7)

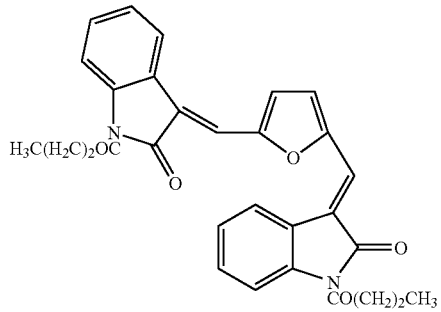

EXAMPLE 11

For the purpose of identifying novel Pim-1 kinase inhibitors, by using an in vitro system for measurement of Pim-1 kinase (see below), inhibitor candidate compounds were searched from a serine/threonine kinase inhibitory compound library (available from ChemDiv). Based on the information of correlation of structural activity of the obtained candidate compounds, synthesis of more than 55 types of compounds were carried out and 6 novel compounds (1), (2), (3), (9), (10) and (7) shown in Table 1 were obtained.

The sensitivity (IC50: inhibitory concentration of 50% of activity) and concentration dependence of these novel compounds to inhibition of Pim-1 activity were studied (using the following system). As shown in FIG. 1, the novel compounds (1) and (2) showed a concentration-dependent inhibitory effect in a range of 1 nM to 100 nM, the compound (3) showed the effect in a range of 0.1 μM to 10 μM, the compounds (9) and (10) showed the effect in a range of 0.15 μM to 5 μM, and the compound (7) showed the effect in a range of 0.0078 μM to 1 μM. The 50% inhibitory concentration (IC50) of the compounds (1), (2), (3), (9), (10) and (7) were 50 nM, 10 nM, 0.8 μM, 1.4 μM, 0.58 μM, and 0.026 μM, respectively, and it was revealed that the compounds inhibit the Pim-1 kinase activity at a low concentration.

In Vitro System for Measurement of Pim-1 Kinase Activity:

(1) Add a biotinylated p21 peptide (1 mM) as a substrate to be phosphorylated by Pim-1 and a recombinant GST-Pim-1 kinase (18 μg/ml) to a kinase buffer.

(2) Add a test compound (dissolved in 2% DMSO) or 2% DMSO (a solvent control) thereto.

(3) Add ATP (10 μM) thereto and incubate the mixture at 25° C. for 30 minutes (initiate a kinase reaction).

(4) Add EDTA (10 mM) thereto to stop the reaction.

(5) Add 10 μl of the kinase reaction mixture to a 96-well plate (which has been blocked in advance) coated with avidin, and incubate the plate at room temperature for 60 minutes.

(6) Wash the wells with a washing buffer three times.

(7) Add a diluted solution (1:500) of an antibody which recognizes phosphorylated p21 (Thr145) to the wells in an amount of 100 μl per well and incubate the plate for 90 minutes.

(8) Wash the wells with a washing buffer three times.

(9) Add a diluted solution (1:2000) of a secondary antibody which recognizes peroxidase (HRP) to the wells in an amount of 100 μl per well and incubate the plate for 60 minutes.

(10) Wash the wells with a washing buffer five times.

(11) Add a substrate (TMB) for peroxidase to the wells and incubate the plate for 8 minutes. Then, stop the reaction with 2 M H₂SO₄ and perform the colorimetric determination using a microplate reader (OD450).

Novel Pim-1 Kinase Inhibitory Compounds

TABLE 1

| Sample ID | Structure |
|---|---|
| (1) | 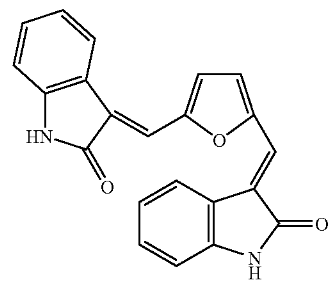 |
| (2) | 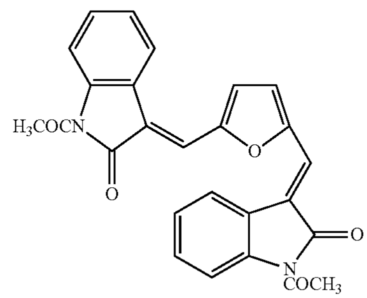 |
| (3) | 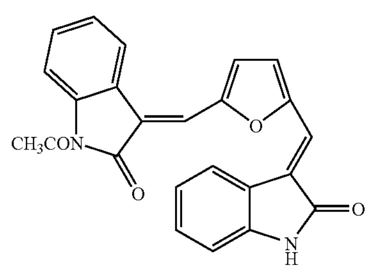 |
| (9) (sodium salt of compound (5)) | 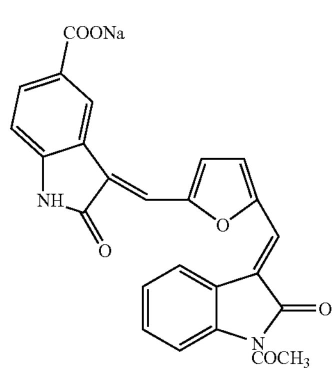 |

TABLE 1-continued

| Sample ID | Structure |
|---|---|
| (10) (sodium salt of compound (6)) | NaOOC-[indolinone]-CH=furan-CH=[indolinone]-COCH₃ |
| (7) | H₃C(H₂C)₂OC-N-[indolinone]=CH-furan-CH=[indolinone]-CO(CH₂)₂CH₃ |

EXAMPLE 12

The cytotoxicity (cell proliferation inhibition and cell lethality) of the compounds (1), (2), (3), (9), (10) and (7) to various cultured cancer cells were studied.

Various cancer cell lines were seeded in 96-well plates at a density of 3 to 5000 cells per well, and on the following day, any of the novel compounds was added thereto such that the final concentrations of the compounds were 0 to 100 μM (the concentration of the solvent DMSO was 0.5%) and the plates were incubated for 24 to 72 hours. The cytotoxicity to cancer cells can be examined by calculating the viable cell count by the MTS method (CellTiter 96 Aqueous One Solution Cell Proliferation Assay, Promega) after incubation.

Here, the MTS method is a viable cell count calculation method using the fact that a tetrazolium compound (MTS) is converted into a chromogenic formazan product by an oxidoreductase of viable cells.

In the measurement method, to each well of a 96-well plate containing 100 μl of a culture medium and sample cells, 20 μl of CellTiter 96 Aqueous One Solution Reagent is added and the plate was incubated in an incubator at 37° C. for 90 to 120 minutes, and then, the absorbance at 490 nm is measured using a 96-well plate reader.

As shown in FIG. 2, the compound (1) showed remarkable cytotoxicity to a pancreatic cancer cell line (MiaPaCa-2), a lung cancer cell line (A549), an oral squamous cell carcinoma cell line (HSC-3), an esophageal squamous cell carcinoma cell line (T.Tn), a uterine cancer cell line (HeLa) and a normal renal cell line (293) at 100 μM and 10 μM, even at 1 μM to some cell lines.

Figure 3:
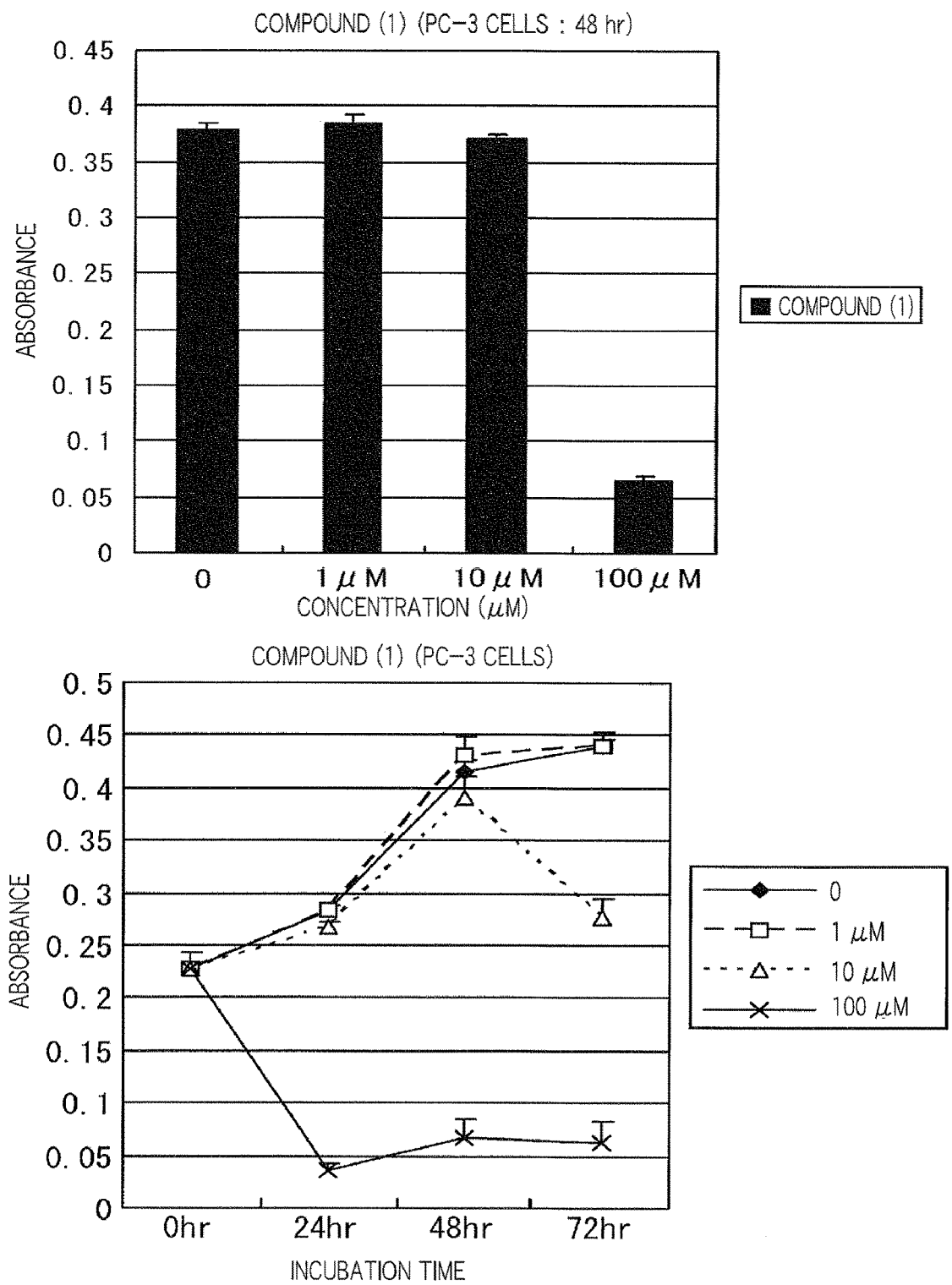
FIG. 3 The bar graph is a view showing the cytotoxicity of the compound (1) to a prostate cancer cell line (PC-3); the horizontal axis indicates the concentration (μM) of the compound; and the vertical axis indicates the absorbance at a wavelength of 490 nm, which shows the viable cell count and represents the cytotoxic activity. The line graph shows the time course observation of the viable cell count; the horizontal axis indicates the time (hr); and the vertical axis indicates the absorbance at a wavelength of 490 nm, which shows the viable cell count and represents the cell lethal effect.
Figure 4A:
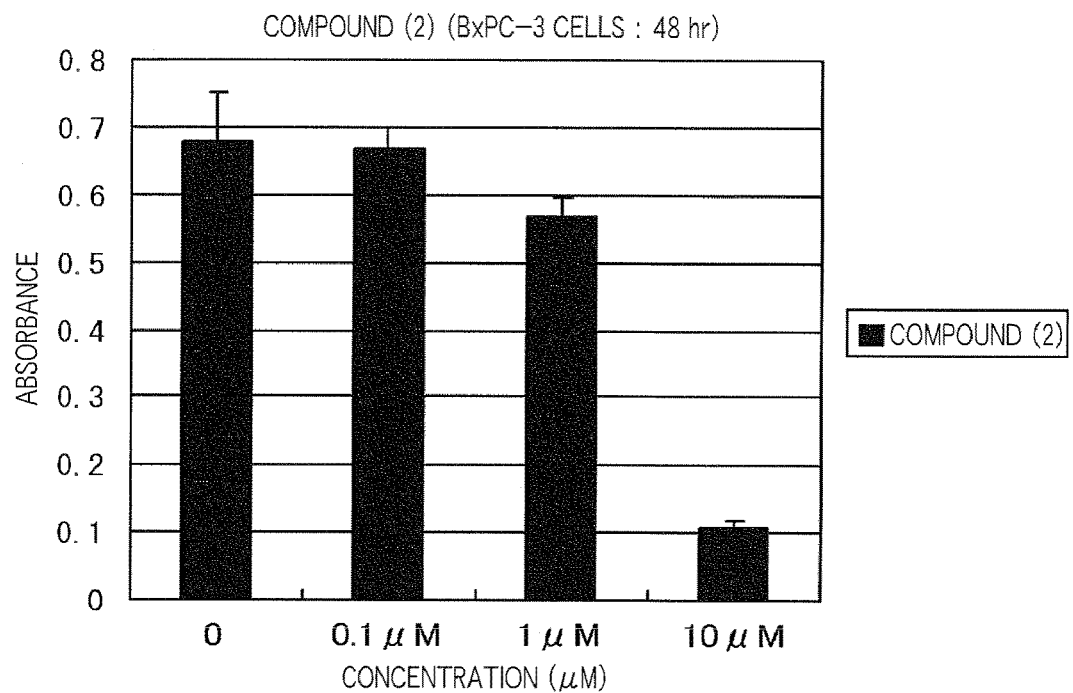
FIG. 4A The bar graph is a view showing the cytotoxicity of the compound (2) to a pancreatic cancer cell line (BxPC-3); the horizontal axis indicates the concentration (μM) of the compound; and the vertical axis indicates the absorbance at a wavelength of 490 nm, which shows the viable cell count and represents the cytotoxic activity. The line graph shows the time course observation of the viable cell count; the horizontal axis indicates the time (hr); and the vertical axis indicates the absorbance at a wavelength of 490 nm, which shows the viable cell count and represents the cell proliferation inhibitory effect and cell lethal effect.
Figure 4A:
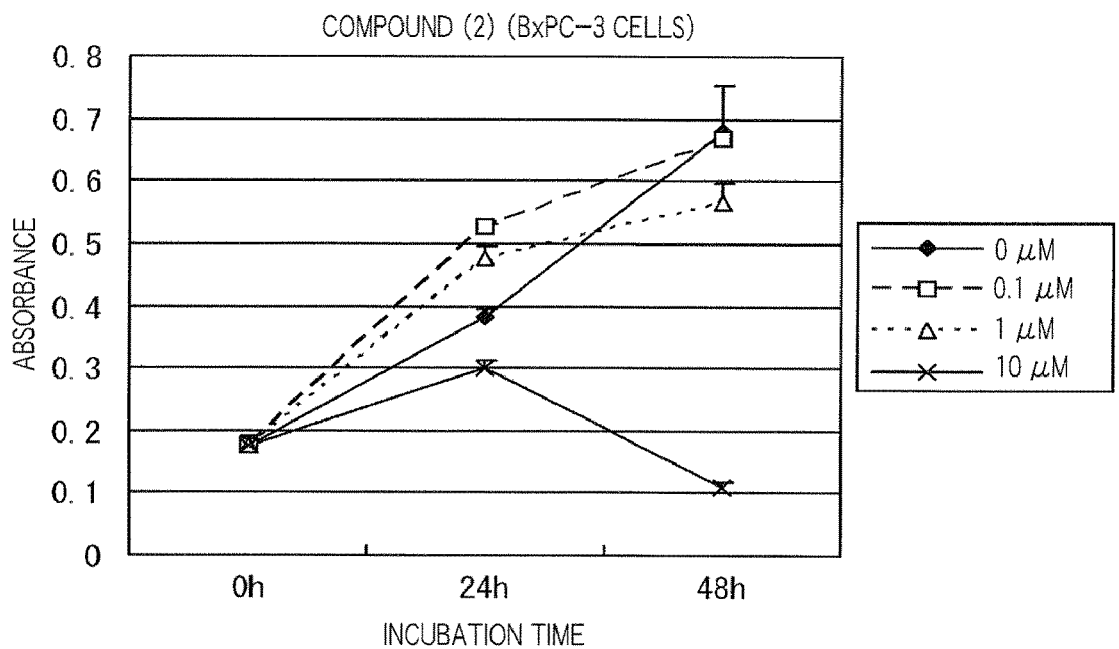
Figure 4B:
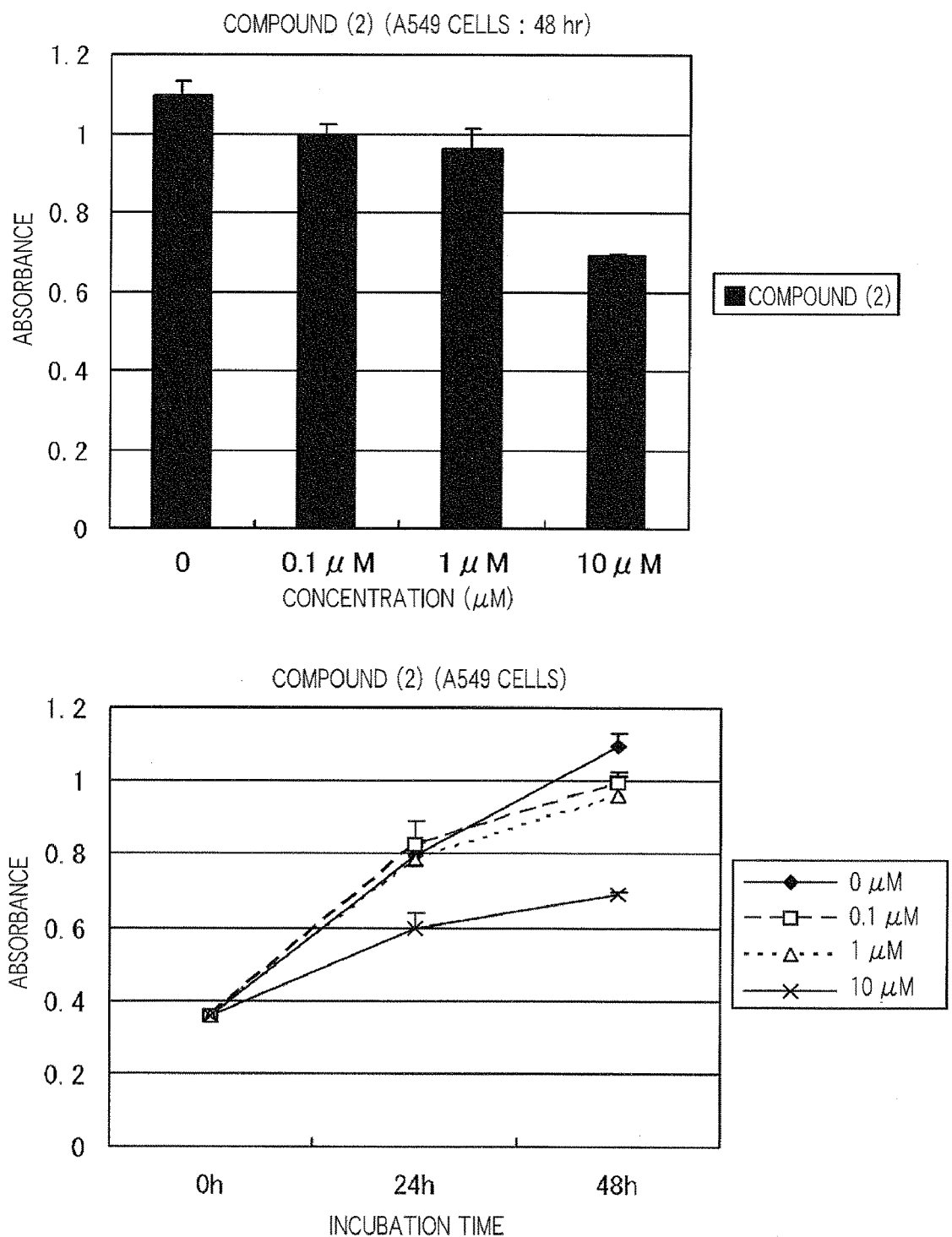
FIG. 4B The bar graph is a view showing the cytotoxicity of the compound (2) to a lung cancer cell line (A549); the horizontal axis indicates the concentration (μM) of the compound; and the vertical axis indicates the absorbance at a wavelength of 490 nm, which shows the viable cell count and represents the cytotoxic activity. The line graph shows the time course observation of the viable cell count; the horizontal axis indicates the time (hr); and the vertical axis indicates the absorbance at a wavelength of 490 nm, which shows the viable cell count and represents the cell proliferation inhibitory effect and cell lethal effect.
Figure 4C:
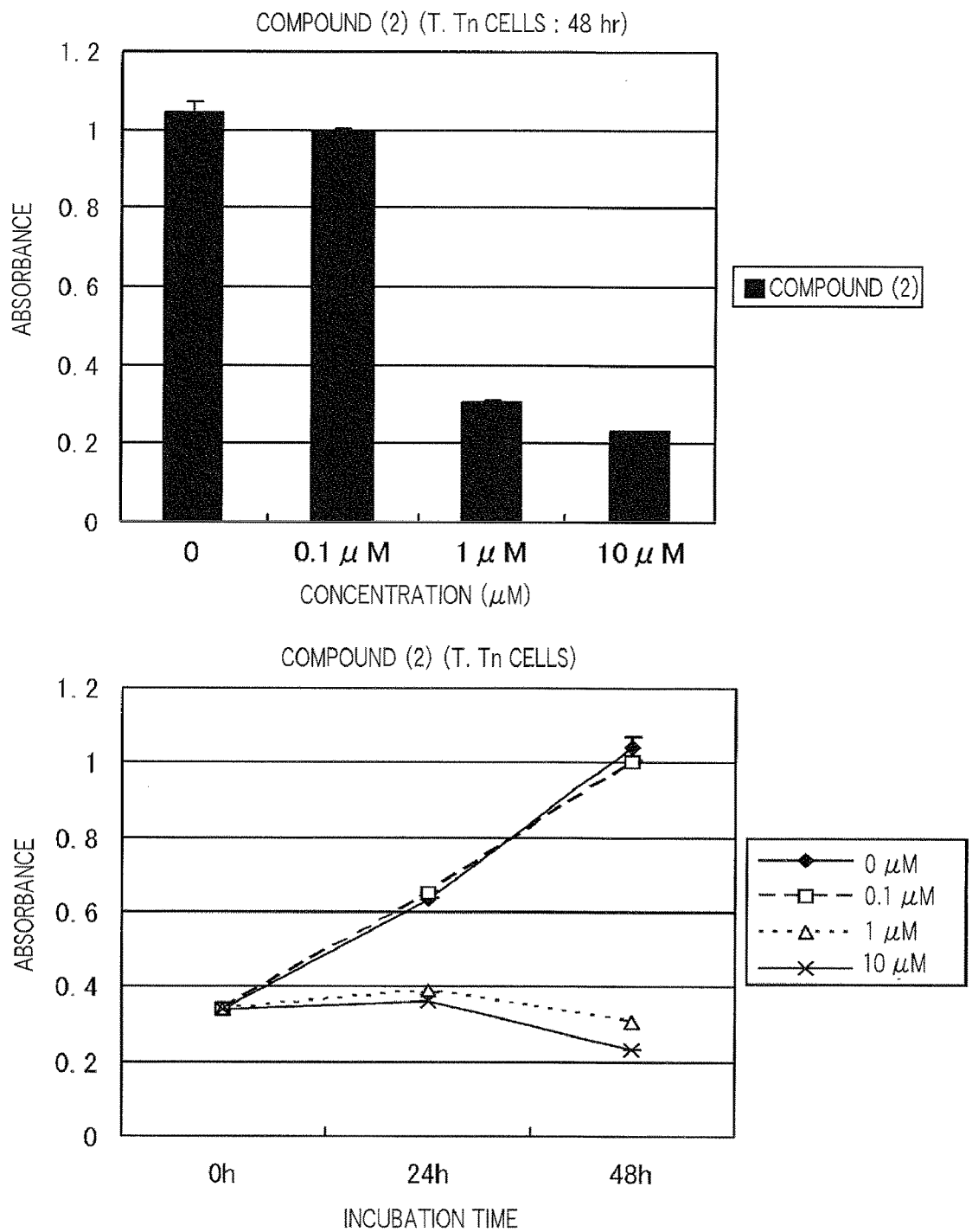
FIG. 4C The bar graph is a view showing the cytotoxicity of the compound (2) to an esophageal squamous cell carcinoma cell line (T.Tn); the horizontal axis indicates the concentration (μM) of the compound; and the vertical axis indicates the absorbance at a wavelength of 490 nm, which shows the viable cell count and represents the cytotoxic effect. The line graph shows the time course observation of the viable cell count; the vertical axis indicates the absorbance at a wavelength of 490 nm, which shows the viable cell count and represents the cell proliferation inhibitory effect and cell lethal effect.

Further, as shown in FIG. 3, it was verified that the compound (1) has a cell lethal effect on a prostate cancer cell line (PC-3) from the time course observation.

Further, as shown in FIG. 4, it was verified that also the compound (2) has a cell proliferation inhibitory effect and a cell lethal effect on a pancreatic cancer cell line (BxPC-3), a lung cancer cell line and an esophageal squamous cell carcinoma cell line.

INDUSTRIAL APPLICABILITY

The compound represented by the above general formula (I) or a pharmaceutically acceptable salt thereof of the invention has an excellent anticancer effect, a kinase inhibitory effect and an ability to induce apoptosis, and therefore is useful as a pharmaceutical, for example, a therapeutic agent or a preventive agent for cancer, cardiac disturbance, myocardial infarction, arteriosclerosis, an occlusive cardiovascular disease, rheumatoid arthritis, diabetic retinopathy, age-related macular degeneration retinopathy, a neurodegenerative disease, an autoimmune disease, an inflammatory disease, diabetes or a viral disease. Further, a kinase inhibitor containing the compound represented by the above general formula (I) as an active ingredient is also useful as a therapeutic or preventive agent for these various diseases.

The invention claimed is:

1. A compound represented by the following general formula (I):

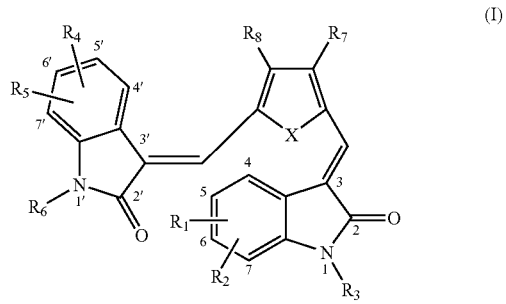

wherein R₁ to R₈ may have a hydrogen atom, a halogen atom, a hydroxy group, a C1-C 6 alkyl group, a C2-C8 alkenyl group, a C1-C6 alkylcarbonyl group or —COOR₉ as a substituent, wherein R₉ represents a hydrogen atom, a C1-C6 alkyl group or a C2-C8alkenyl group; and X represents a sulfur atom, an oxygen atom or NR₁₀, or a pharmaceutically acceptable salt thereof, wherein R₁₀ represents a hydrogen atom, a halogen atom, a hydroxy group, a C1-C6 alkyl group, a C2-C8 alkenyl group or a C1-C6 alkoxy group.

2. The compound or a pharmaceutically acceptable salt thereof according to claim 1, wherein R₁, R₂, R₄ and R₅ are each independently a hydrogen atom or COOR₉, wherein R₉ represents a hydrogen atom, a C1-C6 alkyl group or a C2-C8 alkenyl group.

3. The compound or a pharmaceutically acceptable salt thereof according to claim 1, wherein R₃ and R₆ are each independently a hydrogen atom or a C1-C6 alkylcarbonyl group.

4. The compound or a pharmaceutically acceptable salt thereof according to claim 1, wherein R₇ and R₈ are a hydrogen atom.

5. The compound or a pharmaceutically acceptable salt thereof according to claim 1, wherein X is an oxygen atom.

6. A compound represented by any of the following formulae (1) to (7):

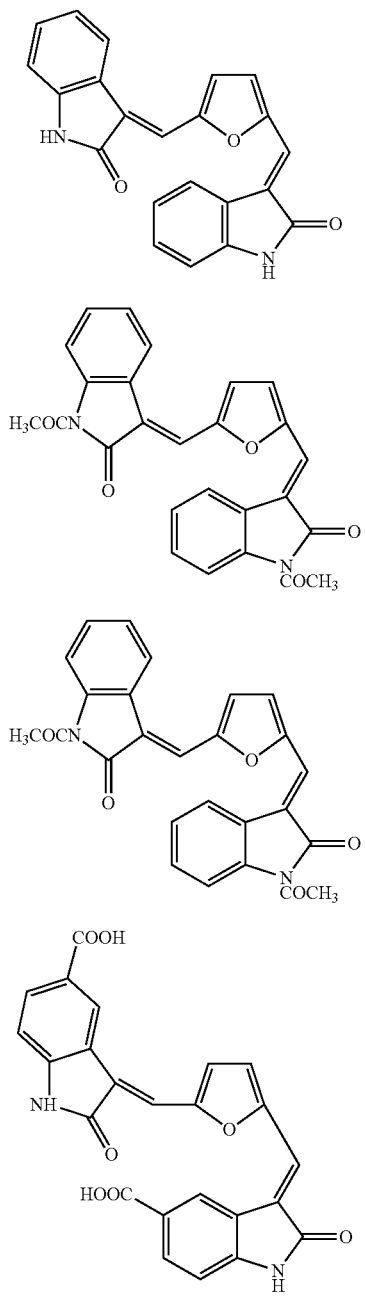

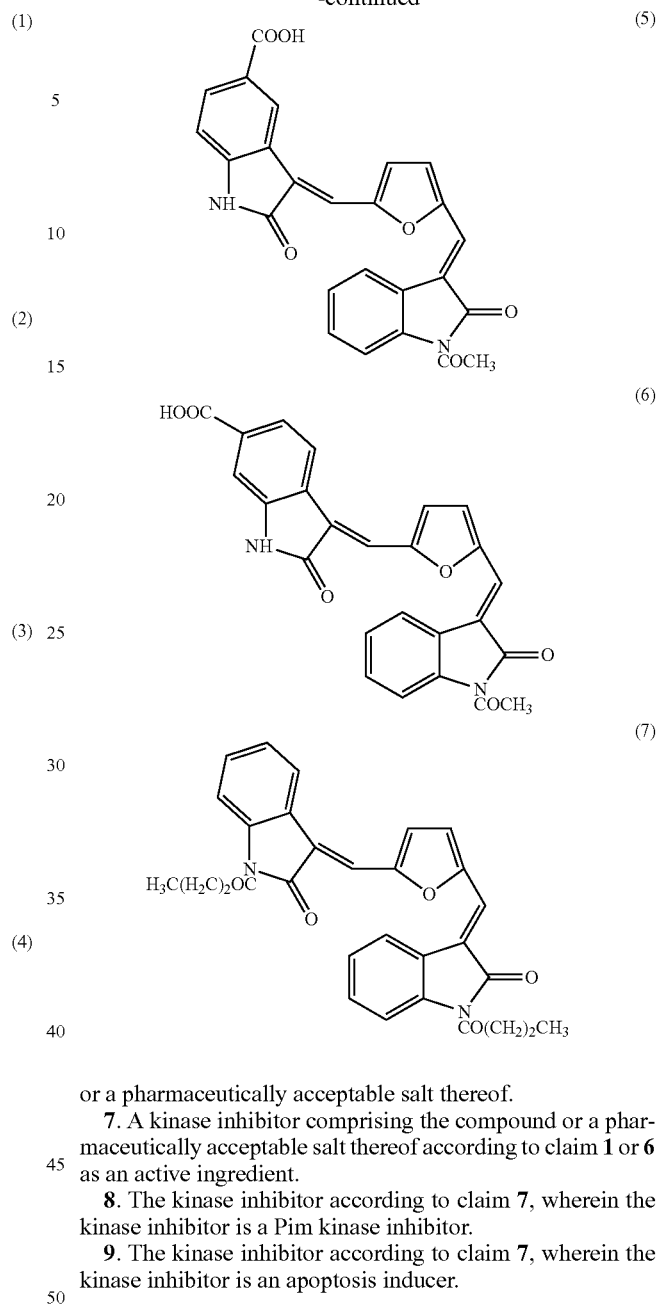

or a pharmaceutically acceptable salt thereof.

7. A kinase inhibitor comprising the compound or a pharmaceutically acceptable salt thereof according to claim 1 or 6 as an active ingredient.

8. The kinase inhibitor according to claim 7, wherein the kinase inhibitor is a Pim kinase inhibitor.

9. The kinase inhibitor according to claim 7, wherein the kinase inhibitor is an apoptosis inducer.

* * * * *